(12) United States Patent
Chen et al.

(10) Patent No.: US 8,106,180 B2
(45) Date of Patent: Jan. 31, 2012

(54) METHODS AND PRODUCTS FOR EXPRESSION OF MICRO RNAS

(75) Inventors: Chang-Zheng Chen, Brookline, MA (US); David Bartel, Brookline, MA (US); Harvey Lodish, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 10/913,288

(22) Filed: Aug. 6, 2004

(65) Prior Publication Data

US 2005/0075492 A1 Apr. 7, 2005

Related U.S. Application Data

(60) Provisional application No. 60/493,239, filed on Aug. 7, 2003.

(51) Int. Cl.
*C07H 21/04* (2006.01)
(52) U.S. Cl. .................................................. 536/24.5
(58) Field of Classification Search ................... 536/24.5
See application file for complete search history.

(56) References Cited

U.S. PATENT DOCUMENTS

| 7,618,814 | B2 * | 11/2009 | Bentwich | 435/320.1 |
| 7,691,995 | B2 * | 4/2010 | Zamore et al. | 536/24.5 |
| 2002/0086356 | A1 | 7/2002 | Tuschl et al. | |
| 2003/0059944 | A1 * | 3/2003 | Lois-Caballe et al. | 435/456 |
| 2003/0108923 | A1 | 6/2003 | Tuschl et al. | |
| 2003/0152559 | A1 * | 8/2003 | Yang et al. | 424/93.21 |
| 2005/0079614 | A1 | 4/2005 | Reinhart et al. | |
| 2005/0144669 | A1 | 6/2005 | Reinhart et al. | |
| 2006/0185027 | A1 | 8/2006 | Bartel et al. | |

FOREIGN PATENT DOCUMENTS

| WO | WO 01/75164 A2 | 10/2001 |
| WO | WO 03/029459 A2 | 4/2003 |
| WO | WO03/093441 A2 * | 11/2003 |
| WO | WO2005/010188 A2 | 2/2005 |
| WO | WO2005/017111 A2 | 2/2005 |

OTHER PUBLICATIONS

Cullen Virus Research 102, 2004, 3-9.*
Bridge, A.J. et al., Induction of an interferon response by RNAi vectors in mammalian cells. Nat. Genet. 34(3): 263-264, 2003.
Chen, Chang-Zheng et al., MicroRNAs modulate hematopoietic lineage differentiation. Science 303: 83-86, 2004.
Gauwerky, C.E. et al., Activation of MYC in a masked t(8;17) translocation results in an aggressive B-cell leukemia. Proc. Natl. Acad. Sci. USA 86: 8867-8871, 1989.
Lagos-Quintana, M. et al., Identification of novel genes coding for small expressed RNAs. Science 294: 853-858, 2001.
Lagos-Quintana, M. et al., Identification of tissue-specific microRNAs from mouse. Current Biology, 12: 735-739, 2002.
Lagos-Quintana, M. et al., New microRNAs from mouse and human. RNA, 9: 175-179, 2003.
Lau, N.C. et al., An Abundant Class of Tiny RNAs with Probable Regulatory Roles in *Caenorhabditis elegans*. Science 294, 858-862, 2001.
Lee, R.C. and Ambros, V. An extensive class of small RNAs in *Caenorhabditis elegans*. Science, 294: 862-864, 2001.
Lim, L.P. et al., The microRNAs of *Caenorhabditis elegans*. Genes & Development, 17(8): 991-1008, 2003.
Lim, L.P. et al., Vertebrate MicroRNA Genes. Science 299: 1540, 2003.
Liu, J. et al., Visualizing and quantifying protein secretion using a Renilla luciferase-GFP fusion protein. Luminescence 15(1):45-49, 2000.
Yekta, S. et al., MicroRNA-directed cleavage of HOXB8 mRNA. Science 304: 594-596, 2004.
Zeng, Y. et al., Both natural and designed micro RNAs can inhibit the expression of cognate mRNAs when expressed in human cells. Mol Cell 9: 1327-1333, 2002.
Reinhart, B.J. et al., MicroRNAs in plants. Genes & Development, 16: 1616-1626, 2002.
Zeng et al., "Efficient Processing of Primary microRNA Hairpins by Drosha Requires Flanking Nonstructured RNA Sequences," *J Bio Chem*, (2005), vol. 280, No. 30, pp. 27595-27603.

* cited by examiner

*Primary Examiner* — Brian Whiteman
(74) *Attorney, Agent, or Firm* — Wolf, Greenfield & Sacks, P.C.

(57) ABSTRACT

The invention relates to microRNAs, methods of producing microRNAs and methods for using microRNAs.

36 Claims, 13 Drawing Sheets

METHODS AND PRODUCTS FOR EXPRESSION OF MICRO RNAS

RELATED APPLICATIONS

This application claims priority to U.S. Provisional Patent Application filed Aug. 7, 2003, entitled "METHODS AND PRODUCTS FOR EXPRESSION OF MICRO RNAs", having Ser. No. 60/493,239 the contents of which are incorporated by reference herein in their entirety.

GOVERNMENT SUPPORT

The invention was supported, in whole or in part, by grant number GM67031 from National Institutes of Health. The Government may have certain rights in the invention.

BACKGROUND OF THE INVENTION

MicroRNAs (miRNAs) are endogenous RNAs, some of which are known to regulate the expression of protein-coding genes at the posttranscriptional level. During miRNA maturation in animals, the primary transcript is first processed to a stem-loop precursor and then the stem-loop is processed to yield a mature miRNA of about 22-nucleotides. These molecules can direct the cleavage of mRNA or they can interfere with productive translation of the mRNA, either of which results in reduced protein accumulation and hence the miRNAs are able to modulate gene expression and related cellular activities. miRNAs are important in development and differentiation, and thus the altered expression of miRNAs could be used to alter development and differentiation during tissue engineering and other applications. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways. This can be a useful tool for studying gene function, human therapies, and other applications. However, current methods for expressing miRNAs, artificial miRNAs, and siRNAs are inefficient and are not effective for many small RNA sequences.

SUMMARY OF THE INVENTION

The present invention relates in part to products and methods of making and using microRNA molecules. In one aspect of the invention a precursor microRNA molecule is provided. The precursor microRNA molecule is an isolated nucleic acid including a stem-loop structure wherein a microRNA sequence is incorporated into the stem-loop structure. The precursor microRNA molecule includes a microRNA flanking sequence on either or both sides of the microRNA sequence.

In an embodiment of the invention the microRNA sequence and the microRNA flanking sequence are derived from the same microRNA gene. In another embodiment of the invention the microRNA sequence and the microRNA flanking sequence are not derived from the same microRNA gene.

In another aspect the invention is a precursor microRNA molecule having a nucleic acid having a stem-loop structure, wherein a microRNA sequence is incorporated into a stem of the stem-loop structure, and, a microRNA flanking sequence flanking at least one end of the stem-loop structure, wherein the microRNA sequence and the microRNA flanking sequence are not derived from the same microRNA gene. Optionally the microRNA sequence is an artificial microRNA.

In one embodiment the precursor microRNA molecule includes at least two stem-loop structures. In another embodiment the microRNA sequences are at least 16-28 nucleotides in length. In another embodiment the microRNA flanking sequences are 40-4,000 or 40-2,000 nucleotides in length. In yet another embodiment the microRNA flanking sequences are at least 40 nucleotides in length.

In yet another embodiment the precursor microRNA molecule has the following nucleic acid sequence

SEQ ID NO.: 23

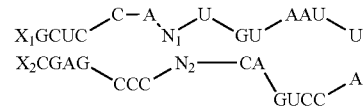

wherein $X_1$, and $X_2$ are nucleotides and wherein $N_1$ and $N_2$ are nucleic acids of 16-28 nucleotides in length and $N_1$ and $N_2$ have at least partial complementarity. $X_1$ and $X_2$ may each be at least 40 nucleotides.

The precursor microRNA molecule in some embodiments has microRNA flanking sequences flanking each end of the stem-loop structure.

Another aspect of the invention provides a method of altering the productive utilization of a target mRNA. The method includes contacting a cell with a vector capable of expressing a precursor microRNA wherein the microRNA sequence is capable of altering the productive utilization of the target mRNA, either by specifying the cleavage of the target mRNA or by altering the accumulation of the protein of the target mRNA through another mechanism, such as translation repression. In one embodiment the precursor microRNA is specific for a cancer-associated RNA. In another embodiment the precursor microRNA is specific for a viral RNA.

In one embodiment the method of contacting a cell with a vector capable of expressing a precursor microRNA wherein the microRNA sequence is capable of altering the productive utilization of a target mRNA is performed in vivo. In another embodiment the method is performed in a subject having cancer. In yet another embodiment the method is performed in a subject having an infection.

In another aspect of the invention a method of altering the productive utilization of a target mRNA including contacting a cell with a vector capable of expressing a mature microRNA that is not naturally expressed in the cell is provided. The mature microRNA is expressed at a level sufficient to cause at least a 2-fold reduction in the accumulation of a protein from the target mRNA of the target protein. In other embodiments it is at least a 5-fold, 10-fold, 20-fold, or 30 fold reduction.

A method of altering productive utilization of a target mRNA in primary cells is also provided. The method involves contacting a primary cell with a vector capable of expressing a mature microRNA that is not naturally expressed in the cell, wherein the mature microRNA is expressed at a level sufficient to cause a reduction in accumulation of a protein from the target mRNA in the primary cell. In one embodiment the primary cell is in vivo.

A method for modulating hematopoiesis is also provided. The method involves contacting a hematopoietic cell with a vector capable of expressing a precursor microRNA, wherein the precursor microRNA includes a microRNA sequence capable of altering accumulation of a protein involved in hematopoiesis.

In yet another aspect of the invention a composition including a vector for producing a precursor microRNA is provided.

The vector includes a sequence encoding a precursor microRNA, including microRNA flanking sequences and at least one promoter element. In one embodiment the promoter is an inducible or tissue specific promoter.

In one embodiment the vector is a viral vector. In a second embodiment the vector is a retroviral vector. In another embodiment the vector includes the nucleic acid sequence of SEQ ID NO. 1 or variants thereof.

One aspect of the invention includes a host cell transfected with a vector capable of producing a precursor microRNA.

Another aspect of the invention encompasses a method for detecting precursor microRNA expression. The precursor microRNA is incorporated into a reporter system. This composition is transfected into a host cell. The expression of a reporter gene product is detected to detect the expression of precursor microRNA by its effect on the accumulation of the protein corresponding to the target mRNA. In one embodiment the reporter system includes a firefly luciferase reporter gene.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

The present invention may be more easily and completely understood when taken in conjunction with the accompanying figures.

DETAILED DESCRIPTION

Figure 1:
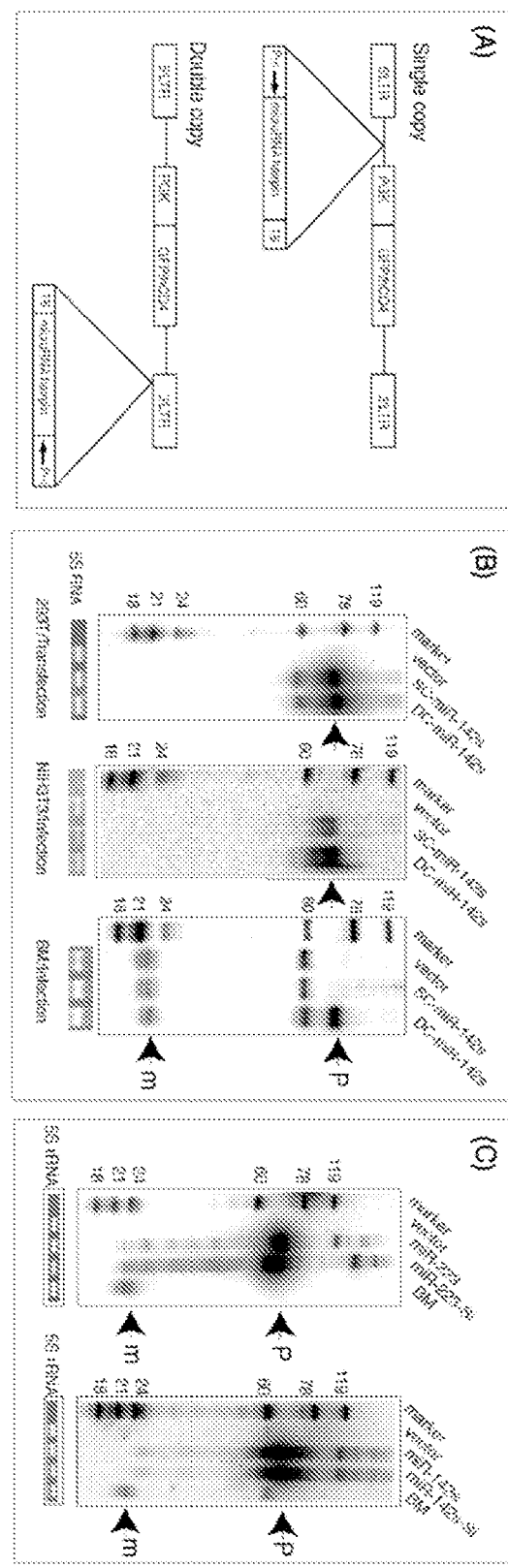
FIG. 1. (a) Retroviral vectors for efficient expression of microRNA hairpins. (b) Northern analysis of the expression of a ~70-nucleotide miR-132s hairpin from the single-copy (SC-miR-132s) or double-copy (DC-miR-132s) constructs. (c) Northern analysis of the expression of exact microRNA hairpin using single copy and double-copy retroviral constructs.

MicroRNAs (which are defined in more detail later as including siRNAs and artificial microRNAs as well as endogenous microRNAs) have potential for use as therapeutics as well as research tools, e.g. analyzing gene function. Although these molecules have potential, one limitation associated with these molecules is the difficulty in expressing adequate quantities of functional mature microRNA. The invention relates, in some aspects, to methods for producing mature microRNA in sufficient quantities for therapeutic and research applications.

The methods for efficient expression of microRNA involve the use of a precursor microRNA molecule having a microRNA sequence in the context of microRNA flanking sequences. The precursor microRNA is composed of any type of nucleic acid based molecule capable of accommodating the microRNA flanking sequences and the microRNA sequence. Examples of precursor microRNAs and the individual components of the precursor (flanking sequences and microRNA sequence) are provided herein. The invention, however, is not limited to the examples provided. The invention is based, at least in part, on the discovery of an important component of precursor microRNAs, that is, the microRNA flanking sequences. The nucleotide sequence of the precursor and its components may vary widely.

In one aspect a precursor microRNA molecule is an isolated nucleic acid including microRNA flanking sequences and having a stem-loop structure with a microRNA sequence incorporated therein. An "isolated molecule" is a molecule that is free of other substances with which it is ordinarily found in nature or in vivo systems to an extent practical and appropriate for its intended use. In particular, the molecular species are sufficiently free from other biological constituents of host cells or if they are expressed in host cells they are free of the form or context in which they are ordinarily found in nature. For instance, a nucleic acid encoding a precursor microRNA having homologous microRNA sequences and flanking sequences may ordinarily be found in a host cell in the context of the host cell genomic DNA. An isolated nucleic acid encoding a microRNA precursor may be delivered to a host cell, but is not found in the same context of the host genomic DNA as the natural system. Alternatively, an isolated nucleic acid is removed from the host cell or present in a host cell that does not ordinarily have such a nucleic acid sequence. Because an isolated molecular species of the invention may be admixed with a pharmaceutically-acceptable carrier in a pharmaceutical preparation or delivered to a host cell, the molecular species may comprise only a small percentage by weight of the preparation or cell. The molecular species is nonetheless isolated in that it has been substantially separated from the substances with which it may be associated in living systems.

An "isolated precursor microRNA molecule" is one which is produced from a vector having a nucleic acid encoding the precursor microRNA. Thus, the precursor microRNA produced from the vector may be in a host cell or removed from a host cell. The isolated precursor microRNA may be found within a host cell that is capable of expressing the same precursor. It is nonetheless isolated in that it is produced from a vector and, thus, is present in the cell in a greater amount than would ordinarily be expressed in such a cell.

The term "nucleic acid" is used to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). The term shall also include polynucleosides (i.e. a polynucleotide minus the phosphate) and any other organic base containing polymer. Purines and pyrimidines include but are not limited to adenine, cytosine, guanine, thymidine, inosine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art. Thus, the term nucleic acid also encompasses nucleic acids with substitutions or modifications, such as in the bases and/or sugars.

"MicroRNA flanking sequence" as used herein refers to nucleotide sequences including microRNA processing elements. MicroRNA processing elements are the minimal nucleic acid sequences which contribute to the production of mature microRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure.

Thus, in some embodiments the flanking sequences are 5-4,000 nucleotides in length. As a result, the length of the precursor molecule may be, in some instances at least about 150 nucleotides or 270 nucleotides in length. The total length of the precursor molecule, however, may be greater or less than these values. In other embodiments the minimal length of the microRNA flanking sequence is 10, 20, 30, 40, 50, 60, 70, 80, 90, 100, 150, 200 and any integer there between. In other embodiments the maximal length of the microRNA flanking sequence is 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

The microRNA flanking sequences may be native microRNA flanking sequences or artificial microRNA flanking sequences. A native microRNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. The artificial microRNA flanking sequences may be flanking sequences found naturally in the context of other microRNA sequences. Alternatively they may be composed of minimal microRNA processing elements which are found within naturally occurring flanking sequences and inserted into other random nucleic acid sequences that do not naturally occur as flanking sequences or only partially occur as natural flanking sequences.

The microRNA flanking sequences within the precursor microRNA molecule may flank one or both sides of the stem-loop structure encompassing the microRNA sequence. Thus, one end (i.e., 5') of the stem-loop structure may be adjacent to a single flanking sequence and the other end (i.e., 3') of the stem-loop structure may not be adjacent to a flanking sequence. Preferred structures have flanking sequences on both ends of the stem-loop structure. The flanking sequences may be directly adjacent to one or both ends of the stem-loop structure or may be connected to the stem-loop structure through a linker, additional nucleotides or other molecules.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches.

In some instances the precursor microRNA molecule may include more than one stem-loop structure. The multiple stem-loop structures may be linked to one another through a linker, such as, for example, a nucleic acid linker or by a microRNA flanking sequence or other molecule or some combination thereof.

An example of a precursor microRNA is the following:
An example of a precursor microRNA is the following:

SEQ ID NO.: 23

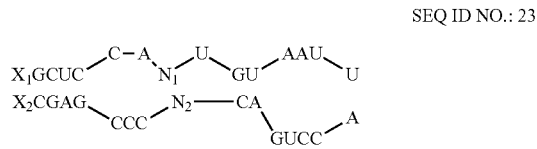

wherein $X_1$, and $X_2$ are nucleotides and wherein $N_1$ and $N_2$ are nucleic acids of 16-28 nucleotides in length. Such a structure is a single example. As described herein the actual nucleotide sequence of the precursor molecule can vary significantly. In general, $X_1$, and $X_2$ refers to the microRNA flanking sequences and $N_1$ and $N_2$ refers to the microRNA sequence and the corresponding sequence that is often degraded and sometimes referred to as microRNA*.

$N_1$ and $N_2$ have at least partial complementarity. "Partial complementarity" when used in this context refers to at least a portion of the nucleic acid sequences that are capable of base pairing. For instance, in some embodiments two nucleic acid sequences that have partial complementarity have at least 10 nucleotides that are capable of base pairing. In some instances, at least 15 nucleotides in each sequence are capable of participating in a base paring interaction with one another. In other instances, the two nucleic acids are perfectly complementary, and thus all nucleotides in each sequence are capable of base pairing with a corresponding nucleotide in the other nucleic acid sequence.

A microRNA sequence is incorporated into the stem-loop structure of the precursor microRNA molecule. As used herein, the term "microRNA" refers to any type of interfering RNA, including but not limited to, endogenous microRNA and artificial microRNA. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). Thus a microRNA sequence is a nucleic acid composed of any one or more of these sequences. MicroRNA sequences have been described in publications such as, Lim, et al., Genes & Development, 17, p. 991-1008 (2003), Lim et al Science 299, 1540 (2003), Lee and Ambrose Science, 294, 862 (2001), Lau et al., Science 294, 858-861 (2001), Lagos-Quintana et al, Current Biology, 12, 735-739 (2002), Lagos-Quintana et al, Science 294, 853-857 (2001), and Lagos-Quintana et al, RNA, 9, 175-179 (2003), which are incorporated by reference. Multiple microRNAs may also be incorporated into the precursor molecule.

The term "productive utilization of mRNA" refers to any change within the cell resulting in less protein accumulating from the mRNA. For instance a compound that interferes with translation of mRNA, would be a compound that modulates productive utilization of mRNA. Similarly, a compound that specifies the cleavage of an mRNA would be a compound that modulates productive utilization of that mRNA.

In some instances, the precursor microRNA includes a microRNA sequence and a microRNA flanking sequence that are derived from the same microRNA gene and in other instances it includes a microRNA sequence and a microRNA flanking sequence that are not derived from the same microRNA gene. The term "that is derived from the same microRNA gene" refers to a nucleic acid sequence that includes both the microRNA sequence and the microRNA flanking sequence(s) that is identical to a nucleic acid found in nature. The term "that is not derived from the same microRNA gene" refers to a nucleic acid sequence that includes both the microRNA sequence and the microRNA flanking sequence(s) and that is not identical to a nucleic acid found in nature. Thus, in some instances, the precursor microRNA will include a flanking microRNA sequence that is not ordinarily associated in nature with the microRNA with which it is associated in the precursor molecule. An artificial microRNA will always, for instance, not be derived from the same microRNA gene as the flanking sequence with which it is associated. Additionally, even if a microRNA sequence and a microRNA flanking sequence are found within a common gene in nature, a precursor microRNA molecule according to the invention is said to include a microRNA sequence and a microRNA flanking sequence that are not derived from the same gene, if the structure of the precursor is modified in any way from that which is ordinarily found in nature, i.e. a nucleotide is changed from a naturally occurring nucleotide or an additional nucleotide (s) or linker is inserted, etc.

In some instances the precursor microRNAs described herein do not include bantam microRNA sequences and flanking sequences. In other instances bantam microRNA sequences and/or flanking sequences are included within the compounds and methods of the invention.

A precursor microRNA molecule may be processed in vivo or in vitro to produce a mature microRNA. A precursor microRNA molecule is processed in a host cell by a ribonuclease enzyme or enzymes. One example of a ribonuclease enzyme which processes precursor microRNA molecules is the RNase II ribonuclease Dicer.

A mature microRNA is a functional microRNA which is capable of modulating or altering the productive utilization of mRNA, i.e., regulating the expression of protein-coding genes at the post-transcriptional level. These methods are described in more detail below. Mature microRNAs generally have a length of between 16 and 28 nucleotides and more often between 21 and 24 nucleotides.

One advantage of the methods and products described herein is the efficient processing of microRNAs. A related advantage is the accuracy of processing. MicroRNAs are generally processed asymmetrically in vivo i.e., only the functional strand is incorporated into a ribonuceoprotein complex-miRNP. This is true for microRNA as well as siRNAs, which are processed into RNA-induced protein complex-RISC. This type of processing is required for the molecule to be functional and stable. The RISC and miRNP are similar, if not identical. Selective incorporation of the functional strand of microRNA, artificial microRNA or siRNA into these protein complexes will increase the efficacy, specificity, and stability of the small RNAs. The rules for selective incorporation of the functional strand into RISC or miRNP are not fully known. But the methods described herein allow selective incorporation of the functional strand into RISC or miRNP and thus result in significantly enhanced production of functional microRNA protein complexes.

The invention also includes vectors for producing precursor microRNA molecules. Generally these vectors include a sequence encoding a precursor microRNA and in vivo expression elements. The in vivo expression elements include at least one promoter. The vector or primary transcript is first processed to produce the stem-loop precursor molecule. The stem-loop precursor is then processed to produce the mature microRNA.

One example of a vector useful for expressing the precursor microRNAs is shown in SEQ ID NO. 1. Thus the invention encompasses the nucleotide sequence of SEQ ID NO 1 as well as variants thereof.

In general, variants typically will share at least 40% nucleotide identity with SEQ ID NO: 1, in some instances, will share at least 50% nucleotide identity; and in still other instances, will share at least 60% nucleotide identity. The preferred variants have at least 70% sequence homology to SEQ ID NO: 1. More preferably the preferred variants have at least 80% and, most preferably, at least 90% sequence homology to SEQ ID NO: 1.

Variants with high percentage sequence homology can be identified, for example, using stringent hybridization conditions. The term "stringent conditions", as used herein, refers to parameters with which the art is familiar. More specifically, stringent conditions, as used herein, refer to hybridization at 65° C. in hybridization buffer (3.5×SSC, 0.02% Ficoll, 0.02% polyvinyl pyrolidone, 0.02% bovine serum albumin, 2.5 mM $NaH_2PO_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65° C. There are other conditions, reagents, and so forth which can be used, which result in a similar degree of stringency.

The "in vivo expression elements" are any regulatory nucleotide sequence, such as a promoter sequence or promoter-enhancer combination, which facilitates the efficient expression of the nucleic acid to produce the precursor microRNA. The in vivo expression element may, for example, be a mammalian or viral promoter, such as a constitutive or inducible promoter or a tissue specific promoter. Constitutive mammalian promoters include, but are not limited to, polymerase promoters as well as the promoters for the following genes: hypoxanthine phosphoribosyl transferase (HPTR), adenosine deaminase, pyruvate kinase, and β-actin. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as in vivo expression element of the invention also include inducible promoters. Inducible promoters are expressed in the presence of an inducing agent. For example, the metallothionein promoter is induced to promote transcription in the presence of certain metal ions. Other inducible promoters are known to those of ordinary skill in the art.

In general, the in vivo expression element shall include, as necessary, 5' non-transcribing and 5' non-translating sequences involved with the initiation of transcription. They optionally include enhancer sequences or upstream activator sequences as desired.

Vectors include, but are not limited to, plasmids, phagemids, viruses, other vehicles derived from viral or bacterial sources that have been manipulated by the insertion or incorporation of the nucleic acid sequences for producing the precursor microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One can readily employ other vectors not named but known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Genetically altered retroviral expression vectors have general utility for the high-efficiency transduction of nucleic acids in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Cliffton, N.J. (1991).

The invention also encompasses host cells transfected with these vectors. Host cells include for instance, cells and cell lines, e.g. prokaryotic (e.g., *E. coli*), and eukaryotic (e.g., dendritic cells, CHO cells, COS cells, yeast expression systems and recombinant baculovirus expression in insect cells).

The precursor microRNA, and subsequently the mature functional microRNAs are useful for altering accumulation of one or more target proteins. This may be accomplished by contacting a cell with a vector capable of expressing a precursor microRNA as described herein. The vector produces the microRNA transcript, which is then processed into precursor microRNA in the cell, which is then processed to produce the mature functional microRNA which is capable of altering accumulation of the target protein. Accumulation of the protein may be effected in a number of different ways. For instance the microRNA may directly or indirectly affect translation or may result in cleavage of the mRNA transcript or even effect stability of the protein being translated from the target mRNA. MicroRNA may function through a number of different mechanisms. The methods and products of the invention are not limited to any one mechanism. The method may be performed in vitro, e.g., for studying gene function, ex vivo or in vivo, e.g. for therapeutic purposes.

An "ex vivo" method as used herein is a method which involves isolation of a cell from a subject, manipulation of the cell outside of the body, and reimplantation of the manipulated cell into the subject. The ex vivo procedure may be used on autologous or heterologous cells, but is preferably used on autologous cells. In preferred embodiments, the ex vivo method is performed on cells that are isolated from bodily fluids such as peripheral blood or bone marrow, but may be isolated from any source of cells. When returned to the subject, the manipulated cell will be programmed for cell death or division, depending on the treatment to which it was exposed. Ex vivo manipulation of cells has been described in several references in the art, including Engleman, E. G., 1997, *Cytotechnology*, 25:1; Van Schooten, W., et al., 1997, *Molecular Medicine Today*, June, 255; Steinman, R. M., 1996, *Experimental Hematology*, 24, 849; and Gluckman, J. C., 1997, *Cytokines, Cellular and Molecular Therapy*, 3:187. The ex vivo activation of cells of the invention may be performed by routine ex vivo manipulation steps known in the art. In vivo methods are also well known in the art. The invention thus is useful for therapeutic purposes and also is useful for research purposes such as testing in animal or in vitro models of medical, physiological or metabolic pathways or conditions.

The ex vivo and in vivo methods are performed on a subject. A "subject" shall mean a human or non-human mammal, including but not limited to, a dog, cat, horse, cow, pig, sheep, goat, primate, rat, and mouse.

In some instances the mature microRNA is expressed at a level sufficient to cause at least a 2-fold or in some instances a 10 fold reduction in accumulation of the target protein. The level of accumulation of a target protein may be assessed using routine methods known to those of skill in the art. For instance, protein may be isolated from a target cell and quantitated using Western blot analysis or other comparable methodologies, optionally in comparison to a control. Protein levels may also be assessed using reporter systems or fluorescently labeled antibodies. In other embodiments, the mature microRNA is expressed at a level sufficient to cause at least a 2, 5, 15, 20, 25, 30, 35, 40, 45, 50, 55, 60, 65, 70, 75, or 100 fold reduction in accumulation of the target protein. The "fold reduction" may be assessed using any parameter for assessing a quantitative value of protein expression. For instance, a quantitative value can be determined using a label i.e. fluorescent, radioactive linked to an antibody. The value is a relative value that is compared to a control or a known value.

Different microRNA sequences have different levels of expression of mature microRNA and thus have different effects on target mRNA and/or protein expression. For instance, in some cases a microRNA may be expressed at a high level and may be very efficient such that the accumulation of the target protein is completely or near completely blocked. In other instances the accumulation of the target protein may be only reduced slightly over the level that would ordinarily be expressed in that cell at that time under those conditions in the absence of the mature microRNA. Complete inhibition of the accumulation of the target protein is not essential for therapeutic purposes. In many cases partial or low inhibition of accumulation may produce a preferred phenotype. The actual amount that is useful will depend on the particular cell type, the stage of differentiation, conditions to which the cell is exposed, the modulation of other target proteins, etc.

The microRNAs may be used to knock down gene expression in vertebrate cells for gene-function studies, including target-validation studies during the development of new pharmaceuticals, as well as the development of human disease models and therapies, and ultimately, human gene therapies.

The methods of the invention are useful for treating any type of "disease", "disorder" or "condition" in which it is desirable to reduce the expression or accumulation of a particular target protein(s). Diseases include, for instance, but are not limited to, cancer, infectious disease, cystic fibrosis, blood disorders, including leukemia and lymphoma, spinal muscular dystrophy, early-onset Parkinsonism (Waisman syndrome) and X-linked mental retardation (MRX3).

The microRNAs are useful in research and therapeutics related to hematopoiesis. During hematopoiesis at least eight distinct lineages of mature blood cells are formed as the descendents of the multipotential hematopoietic stem cells (HSCs). Hematopoietic stem cells first arise within the extra-embryonic yolk sac and later the aortic-gonad-mesonephros (AGM) region of the developing embryo. Thereafter hematopoiesis normally occurs in the fetal liver and in adult bone marrow. In the adult certain stresses induce extramedullary hematopoiesis, especially in the spleen. Hematopoiesis is sustained for life by self-renewal of the HSCs and their continuous development into all blood cells types. The extraordinary ability of HSCs to self-renew and differentiate was demonstrated by the repopulation of the entire blood system of a mouse by a single stem cell. Because of their ability to self-renew and to differentiate into all blood cells, HSCs form the basis of bone marrow transplantation for treatment of leukemias and other cancers and several nonmalignant blood cell disorders.

In order to identify microRNAs that might play roles in hematopoiesis, microRNAs were cloned from mouse bone marrow, the primary adult hematopoietic organ in vertebrates. 2180 tiny RNAs isolated from mouse bone marrow were cloned and sequenced. These represented about 100 unique microRNA. These hematopoietic microRNAs are listed in Table 1. Nineteen frequently cloned microRNAs shown in Table 2 were subjected to further analysis. These included 15 previously identified microRNAs and 4 newly identified microRNAs. All but two of these microRNAs (LM3_A01-3 and miR-191) were perfectly conserved in the human genome.

TABLE 1

Some of the microRNAs frequently cloned from mouse bone marrow. Some microRNAs were represented by clones of different lengths, due to heterogeneity at the microRNA 3' terminus. The observed size range is indicated, as is the microRNA sequence of the most abundant length.

| microRNASeq. Id | microRNA sequence | Size range | # of clones | Location | begin | end |
|---|---|---|---|---|---|---|
| let-7c LM2_B07-1 | (SEQ ID NO: 7) UGAGGUAGUAGGUUGUAUGGUU | 22-23 | 12 | CONTIG_128829 | 246 | 267 |
| let-7g LP1_B02-8 | (SEQ ID NO: 8) UGAGGUAGUAGUUUGUACAGU | 20-23 | 11 | CONTIG_265484 | 2018 | 2038 |
| miR-15a B1_F06-2 | (SEQ ID NO: 9) UAGCAGCACAUAAUGGUUUGUG | 21-22 | 4 | CONTIG_87894 | 853 | 832 |

TABLE 1-continued

Some of the microRNAs frequently cloned from mouse bone marrow.
Some microRNAs were represented by clones of different lengths, due to
heterogeneity at the microRNA 3' terminus. The observed size range is
indicated, as is the microRNA sequence of the most abundant length.

| microRNA | Seq. Id | microRNA sequence | Size range | # of clones | Location | begin | end |
|---|---|---|---|---|---|---|---|
| miR-16 | B1_D01-3 | (SEQ ID NO: 10) UAGCAGCACGUAAAUAUUGGCG | 21-25 | 34 | CONTIG_87894 | 713 | 693 |
| miR-19b | LM1_B07-3 | (SEQ ID NO: 11) UGUGCAAAUCCAUGCAAAACUGA | 21-23 | 9 | CONTIG_347954 | 1756 | 1778 |
| miR-20 | LM1_B03-2 | (SEQ ID NO: 12) UAAAGUGCUUAUAGUGCAGGUAG | 22-24 | 18 | Hs13_10023 | 1387067 | 1387089 |
| miR-23a | LP1_B05-2 | (SEQ ID NO: 13) AUCACAUUGCCAGGGAUUUCCA | 21-23 | 5 | CONTIG_548175 | 437 | 458 |
| miR-27b | B2_E07-1 | SEQ ID NO: 13) UUCACAGUGGCUAAGUUCUGC | 20-23 | 7 | Hs9_8633 | 1373759 | 1373779 |
| miR-29a | LM4_A03-3 | (SEQ ID NO: 15) UAGCACCAUCUGAAAUCGGUUA | 22-22 | 20 | Hs7_23805 | 55795 | 55774 |
| miR-30b | B1_B01-2 | (SEQ ID NO: 6) UGUAAACAUCCUACACUCAGCU | 22-23 | 12 | CONTIG_572951 | 1505 | 1384 |
| miR-30c | B1_C07-1 | (SEQ ID NO: 16) UGUAAACAUCCUACACUCUCAGCU | 23-25 | 13 | CONTIG_117246 | 3389 | 3412 |
| miR-104 | B1_D01-7 | (SEQ ID NO: 17) UAGCUUAUCAGACUGAUGUUGAC | 21-24 | 37 | CONTIG_168444 | 1754 | 1732 |
| miR-132s | B1_G04-1 | (SEQ ID NO: 5) CCCAUAAAGUAGAAAGCACUAC | 22-23 | 16 | Hs17_10808 | 2182613 | 2182634 |
| mir-191 | LM1_E02-3 | (SEQ ID NO: 18) CAACGGAAUCCCAAAAGCAGCU | 20-24 | 32 | CONTIG_261531 | 3175 | 3196 |
| miR-223 | B1_E08-6 | (SEQ ID NO: 3) UGUCAGUUUGUCAAAUACCCCAA | 20-24 | 65 | CONTIG_202715 | 440 | 418 |
| new | B1_G08-2 | (SEQ ID NO: 19) UCCUGUACUGAGCUGCCCCGAG | 22-23 | 7 | Hs8_8395 | 132054 | 132033 |
| new | LP1_B02-3 | (SEQ ID NO: 20) UUAUAAAGCAAUGAGACUGAU | 21-22 | 7 | CONTIG_7440 | 8193 | 8213 |
| new | LM3_A01-3 | (SEQ ID NO: 21) UGAGGUAUUAGUUUGUGCUGUUA | 22-24 | 10 | CONTIG_195284 | 13756 | 13734 |
| new | LM4_D05-3 | (SEQ ID NO: 22) UACCACAGGGUAGAACCACGGAC | 17-23 | 8 | Hs16_19764 | 637009 | 636987 |

To identify microRNAs expressed at sites of hematopoiesis, we probed northern blots of RNA isolated from different mouse tissues, including brain, heart, lung, liver, kidney, muscle, fetal liver, bone marrow, spleen, and thymus. Among these tissues, bone marrow, spleen, and thymus represent three major adult hematopoiesis sites. These organs play different roles in adult hematopoiesis and comprise significantly different cell types. Bone marrow, the primary hematopoietic organ in adult vertebrates, provides other secondary hematopoietic organs with committed progenitor cells. It consists of hematopoietic stem cells and myeloid, erythroid and lymphoid cells at a variety of differentiation stages, although most bone marrow cells belong to myeloid and erythroid lineages. Thymus, the primary lymphoid organ, constitutes mainly T-lymphocytes. Spleen, the secondary lymphoid organ, mainly comprises differentiated reticulocytes and T and B lymphocytes. Fetal liver is the embryonic hematopoiesis site. Thus, analysis of microRNA expression in these four tissues reveals not only the hematopoietic-specific microRNAs but also can provide guidance as to their differential roles during hematopoietic development. For 17 of the 19 microRNAs, expression was detected on the Northerns, and each of these had tissue-specific expression patterns (Table 2). For 12 of these microRNAs, expression was readily detected in hematopoietic tissues.

TABLE 3

Summary of tissue and developmental expression of microRNAs cloned from mouse bone marrow. Northern blots of total RNA from a variety of mouse tissues, with a focus on hematopoietic tissues of different functions and developmental stages, were probed for the indicated microRNA. Signal intensities were ranked (−, negative; +, positive; +++++, most positive) after normalization to the U6 signal to compensate for differential sample loading.

| microRNA | Seq. id | Brain | Heart | Lung | Liver | Kidney | Muscle | Fetal liver | Bone marrow | Spleen | Thymus |
|---|---|---|---|---|---|---|---|---|---|---|---|
| miR-15a | B1__F06-2 | − | − | +++ | − | ++ | − | − | + | + | ++ |
| miR-16 | B1__D01-3 | + | + | +++ | + | ++ | + | + | +++ | +++ | +++ |
| miR-20 | LM1__B03-2 | − | − | + | − | − | − | + | +++ | ++ | ++++ |
| miR-132s | B1__G04-1 | − | − | + | − | − | − | + | +++ | +++ | +++ |
| miR-223 | B1__E08-6 | − | − | + | − | − | − | − | ++++ | − | − |
| let-7c | LM2__B07-1 | +++ | ++ | ++++ | − | ++ | + | − | + | + | + |
| let-7g | LP1__B02-8 | + | + | +++ | ++ | ++ | + | − | + | + | + |
| miR-19b | LM1__B07-3 | − | − | + | − | − | − | − | − | − | − |
| miR-23a | LP1__B05-2 | − | + | +++ | − | + | + | − | − | ++ | − |
| miR-27b | B2__E07-1 | − | − | ++++ | − | + | − | − | − | − | − |
| miR-29a | LM4__A03-3 | +++++ | +++ | ++++ | +++ | +++ | ++ | − | + | ++++ | ++ |
| miR-30b | B1__B01-2 | − | − | + | − | + | − | − | − | − | − |
| miR-30c | B1__C07-1 | − | − | + | − | + | − | − | − | − | − |
| miR-104 | B1__D01-7 | − | − | ++++ | +++ | ++ | + | − | + | ++ | + |
| miR-191 | LM1__E02-3 | − | + | − | − | − | − | − | − | − | − |
| new | LP1__B02-3 | − | − | + | + | − | − | − | + | + | − |
| new | B1__G08-2 | + | + | + | − | − | − | − | − | + | − |
| new | LM3__A01-3 | − | − | − | − | − | − | − | − | − | − |
| new | LM4__D05-3 | − | − | − | − | − | − | − | − | − | − |

The following five microRNAs, mir-15a, miR-16, miR-20, miR-132s and miR-223, exhibited high and often preferential accumulation in hematopoietic tissues and were found to be regulated by cytokines.

miR-132s, the microRNA found at a breakpoint of a t(8:17) translocation associated with an aggressive B-cell leukemia, is primarily expressed in hematopoietic tissues (with the lung being the only other tissue with appreciable expression). Significant expression of this microRNA was seen already in E13 fetal liver. The expression of mature miR-132s in bone marrow and spleen was comparable and about 2-fold higher than that in thymus. Interestingly, accumulation of the presumed miR-132 precursor was high, and the ratio of mature and precursor RNAs varied in different tissues, suggesting regulation at the level of Dicer processing.

miR-20 was expressed in a similar pattern as miR-132s, though there was substantially higher accumulation of this microRNA in the thymus compared to the spleen.

miR-223 had the most striking tissue specificity of any of the microRNA examined. It was very strongly expressed in bone marrow, and was detectable in spleen but essentially negative in thymus, E13 fetal liver and all other mouse tissues, except the lung.

miR-16 and miR-15a are the two microRNAs that derive from band 13q13.3 of the human chromosome 13, the site of the most common structural aberrations in both mantle cell lymphoma and B-cell chronic lymphocytic leukemia. Their loci are within 130 bp of each other, suggesting that they might be transcribed and processed from a single primary transcript. Consistent with this idea, they have similar expression patterns, except that miR-16 appears to accumulate to much higher levels. Expression is high in the adult hematopoietic tissues, although these microRNAs, particularly miR-16, can be readily detected in other tissues.

Two of these microRNAs, mir-15a and miR-16, are within band 13q13—a region of human chromosome 13 that is thought to harbor a lymphoid regulatory locus because it is the site of the most common structural aberrations in both mantle cell lymphoma and B-cell chronic lymphocytic leukemia. Another one of the hematopoietic microRNA genes, mir-132, maps to the breakpoint junction of a t(8;17) translocation that has been linked to an aggressive B cell leukemia. In this translocation, a truncated MYC gene is fused to the promoter and 5' portion of the mir-132 gene. This expression data, together with chromosomal aberrations associated with human leukemias, implicate microRNAs in the developmental decisions of hematopoiesis. Thus, the microRNAs are useful in therapeutic protocols related to hematopoeitic disorders including leukemias and lymphomas.

Cancers include but are not limited to biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor.

An infectious disease, as used herein, is a disease arising from the presence of a foreign microorganism in the body. A microbial antigen, as used herein, is an antigen of a microorganism. Microorganisms include but are not limited to, infectious virus, infectious bacteria, and infectious fungi.

Examples of infectious virus include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Examples of infectious bacteria include but are not limited to: *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans.* Other infectious organisms (i.e., protists) include: *Plasmodium* such as *Plasmodium falciparum, Plasmodium malariae, Plasmodium ovale,* and *Plasmodium vivax* and *Toxoplasma gondii.*

In one aspect, the invention provides a method of administering any of the compositions described herein to a subject. When administered, the compositions are applied in a therapeutically effective, pharmaceutically acceptable amount as a pharmaceutically acceptable formulation. As used herein, the term "pharmaceutically acceptable" is given its ordinary meaning. Pharmaceutically acceptable compounds are generally compatible with other materials of the formulation and are not generally deleterious to the subject. Any of the compositions of the present invention may be administered to the subject in a therapeutically effective dose. A "therapeutically effective" or an "effective" as used herein means that amount necessary to delay the onset of, inhibit the progression of, halt altogether the onset or progression of, diagnose a particular condition being treated, or otherwise achieve a medically desirable result, i.e., that amount which is capable of at least partially preventing, reversing, reducing, decreasing, ameliorating, or otherwise suppressing the particular condition being treated. A therapeutically effective amount can be determined on an individual basis and will be based, at least in part, on consideration of the species of mammal, the mammal's age, sex, size, and health; the compound and/or composition used, the type of delivery system used; the time of administration relative to the severity of the disease; and whether a single, multiple, or controlled-release dose regiment is employed. A therapeutically effective amount can be determined by one of ordinary skill in the art employing such factors and using no more than routine experimentation.

The terms "treat," "treated," "treating," and the like, when used herein, refer to administration of the systems and methods of the invention to a subject, which may, for example, increase the resistance of the subject to development or further development of cancers, to administration of the composition in order to eliminate or at least control a cancer or a infectious disease, and/or to reduce the severity of the cancer or infectious disease. When administered to a subject, effective amounts will depend on the particular condition being treated and the desired outcome. A therapeutically effective dose may be determined by those of ordinary skill in the art, for instance, employing factors such as those further described below and using no more than routine experimentation.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day. As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parental administration, in some cases, may be from one to several orders of magnitude lower dose per day, as compared to oral doses. For example, the dosage of an active compound when parentally administered may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day.

In some embodiments, the concentration of the active compound(s), if administered systemically, is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. Preferably, the concentration, if applied topically, is about 0.1 mg to about 500 mg/gm of ointment or other base, more preferably about 1.0 mg to about 100 mg/gm of base, and most preferably, about 30 mg to about 70 mg/gm of base. The specific concentration partially depends upon the particular composition used, as some are more effective than others. The dosage concentration of the composition actually administered is dependent at least in part upon the particular physiological response being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously effect the mammal. The dosage can be determined by one of ordinary skill in the art employing such factors and using no more than routine experimentation.

In the event that the response of a particular subject is insufficient at such doses, even higher doses (or effectively higher doses by a different, more localized delivery route) may be employed to the extent that subject tolerance permits. Multiple doses per day are also contemplated in some cases to achieve appropriate systemic levels within the subject or within the active site of the subject. In some cases, dosing amounts, dosing schedules, routes of administration, and the like may be selected as described herein, whereby therapeutically effective levels for the treatment of cancer are provided.

In certain embodiments where cancers are being treated, a composition of the invention may be administered to a subject who has a family history of cancer, or to a subject who has a genetic predisposition for cancer. In other embodiments, the composition is administered to a subject who has reached a particular age, or to a subject more likely to get cancer. In yet other embodiments, the compositions is administered to subjects who exhibit symptoms of cancer (e.g., early or advanced). In still other embodiments, the composition may be administered to a subject as a preventive measure. In some embodiments, the inventive composition may be administered to a subject based on demographics or epidemiological studies, or to a subject in a particular field or career.

Administration of a composition of the invention to a subject may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active compound(s) of the composition within the subject without causing clinically unacceptable adverse effects.

Any medically acceptable method may be used to administer a composition to the subject. The administration may be localized (i.e., to a particular region, physiological system, tissue, organ, or cell type) or systemic, depending on the condition being treated. For example, the composition may be administered orally, vaginally, rectally, buccally, pulmonary, topically, nasally, transdermally, through parenteral injection or implantation, via surgical administration, or any other method of administration where suitable access to a target is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the active compound. Other oral compositions suitable for use with the invention include solutions or suspensions in aqueous or non-aqueous liquids such as a syrup, an elixir, or an emulsion. In another set of embodiments, the composition may be used to fortify a food or a beverage.

Injections can be e.g., intravenous, intradermal, subcutaneous, intramuscular, or interperitoneal. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

In general, the compositions of the invention may be delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly (ortho)esters, poly(butic acid), poly(valeric acid), and poly (lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In certain embodiments of the invention, the administration of the composition of the invention may be designed so as to result in sequential exposures to the composition over a certain time period, for example, hours, days, weeks, months or years. This may be accomplished, for example, by repeated administrations of a composition of the invention by one of the methods described above, or by a sustained or controlled release delivery system in which the composition is delivered over a prolonged period without repeated administrations. Administration of the composition using such a delivery system may be, for example, by oral dosage forms, bolus injections, transdermal patches or subcutaneous implants. Maintaining a substantially constant concentration of the composition may be preferred in some cases.

Other delivery systems suitable for use with the present invention include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

In some embodiments, the compositions of the invention may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. Those of skill in the art can readily determine the various parameters for preparing and formulating the compositions of the invention without resort to undue experimentation.

In some embodiments, the present invention includes the step of forming a composition of the invention by bringing an active compound into association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product.

In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

The invention also includes methods for quantitating a level of precursor microRNA expression. The method involves incorporating a precursor microRNA into a reporter system, transfecting a host cell with the reporter system, and detecting expression of a reporter gene product to quantitate the level of precursor microRNA expression. In some embodiments the reporter system includes a firefly luciferase reporter gene.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES
Methods

Retroviral Constructs for microRNA expression. We have developed a retroviral vector using the murine stem cell virus (Clonetech) backbone (FIG. 1a). A pol III expression cassette, which consists of the human H1 promoter ($P_{H1}$), the microRNA hairpin and a polyT termination sequence (T5), was placed after the viral 5'LTR resulting in a single copy (SC) of the microRNA, or in the viral 3'LTR whereby viral replication resulted in a double copy (DC) of the microRNA gene (FIG. 1a).

Table of miRNA sequences

| | | | |
|---|---|---|---|
| miR-223 | (SEQ ID NO: 3) B1_E08-6 | UGUCAGUUUGUCAAAUACCCCAA |
| miR-181 | (SEQ ID NO: 4) LM3_A05-1 | AACAUUCAACGCUGUCGGUGA |
| miR-132s | (SEQ ID NO: 5) B1_G04-1 | CCCAUAAAGUAGAAAGCACUAC |
| miR-30 | (SEQ ID NO: 6) B1_B01-2 | UGUAAACAUCCUACACUCAGCU |

Construction of precursor microRNA with flanking sequences. We amplified miR-223 gene segments from mouse genomic DNA with lengths indicated. Each fragment was designed to give rise to a transcript containing the miR-223 minimal hairpin (67 nt) and either 0-, 10-, 20-, 40-, 60-, 80-nucleotide flanking sequences on both sides of the hairpin. microRNA constructs miR-223, miR-181 and miR-132, each designed to produce transcripts of 271-273 nucleotides in length, were also made. These constructs were each cloned into the H1 expression cassette of the double-copy retroviral construct (FIG. 1a). The constructs were transiently transfected into 293T cells and expressed.

Ectopic expression of microRNAs. MicroRNAs were transiently expressed by transfecting double-copy miRNA constructs into a mammalian cell line, i.e. 293T cells. Or, double-copy miRNA constructs were transfected into a retroviral packaging cell line to generate retrovirus, and miRNAs were stably expressed by tranducing miRNA virus into mammalian cells, such as, NIH3T3 or hematopoietic stem/progenitor cells. Expression of candidate microRNA loci was examined using Northern blots and radiolabeled DNA probes. To maintain hybridization specificity without varying hybridization or washing conditions, the length of probes for different sequences was adjusted so that the predicted melting temperatures of the microRNA-probe duplexes did not exceed 60° C. Probes not corresponding to the entire microRNA sequence were designed to hybridize to the 3' region of the microRNA, which is most divergent among related microRNA sequences. The radiolabeled probes against the miRNA, or the miRNA* (the small RNA processed from the opposite arm of the miRNA stem-loop structure) were used to detect corresponding mature RNAs and unprocessed precursors. Ethidium staining of 5S RNA served as a loading control.

Figure 5:
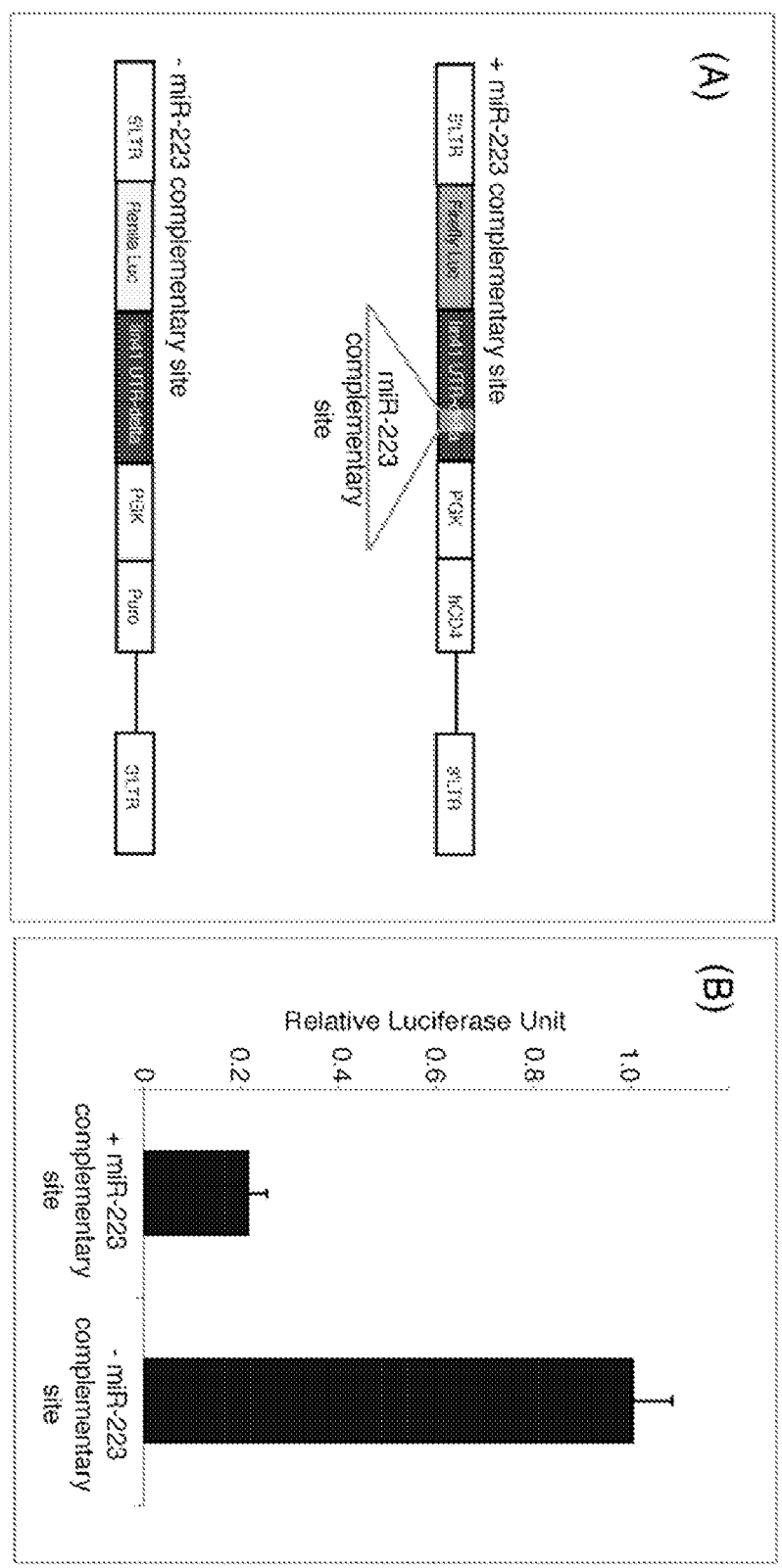
FIG. 5. A luciferase reporter system for testing microRNA-mediated repression in mammalian cells. (a) A schematic diagram of retroviral reporter constructs. (b) A graph to show repression of the target reporter gene by ectopically expressed miR-223 in mammalian cells.

Luciferase reporter system for detection of miRNA-mediated translational repression. The firefly luciferase gene (Promega) was fused to a mutated C. elegans lin-413'UTR (lin-413'UTR-delta, Genebank accession no, AF195610) in which an 80-nt segment containing both let-7 complementary sites (green) was deleted, and replaced with a miR-223 perfect complementary site (FIG. 5a). In a control reporter, the Renilla luciferase gene (Promega) was fused to lin-413'UTR-delta. All luciferase genes were under the control of the viral LTR promotor. To detect translational repression of the luciferase gene, virus was produced by transfecting the constructs into the BOSC23 viral packaging cell line (Pear et al., 1993) and titred by infecting NIH3T3 cells, analyzing CD4 expression using FACS. NIH3T3 cells stably expressing miR-223 or other miRNAs were infected with equal titer of fLuc-lin41UTRdelta+miR-223 target or fLuc-lin41UTRdelta−miR-223 target virus along with control virus rLuc-lin41UTRdelta. Four days after infection, luciferase activity was measured using the luciferase assay (Promega). Firefly luciferase activity was normalized using Renilla luciferase activity.

Figure 7:
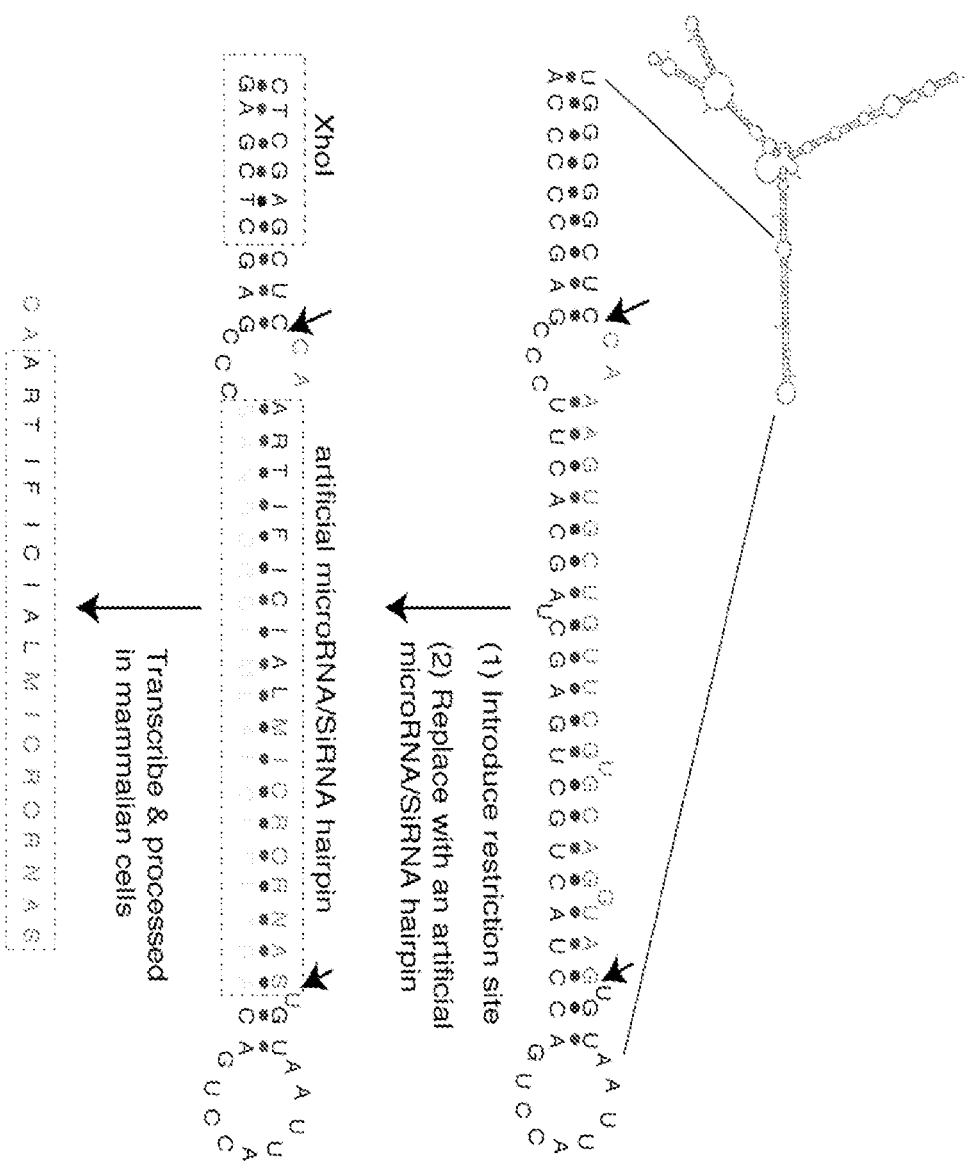
FIG. 7. Schematic diagram of artificial-microRNA/siRNA design (SEQ ID NO.:25 and SEQ ID NO.:26-28; the depicted artificial microRNA/siRNA hairpin is represented in the sequence listing by "n" at residue 12 and its complement is represented by "n" at reside 27).

Construction and expression of artificial microRNA/SiRNA Artificial microRNA (A_miRNAs or siRNAs) were designed to target 21-nucleotide unique sequences in the firefly luciferase gene. These constructs were cloned into the B1_C02-3 microRNA template in a retroviral construct as indicated in FIG. 7. Expression of siRNAs was first tested in 293T cells by transient transfection. Radiolabeled probes against SiLuc311 or SiLuc1276, and their complement strands, SiLuc311* or SiLuc1276* respectively, were used to detect corresponding mature A_miRNAs/siRNAs and unprocessed precursors on Northern blots. Ethidium staining of 5S RNA served as a loading control. Stable cell lines expressing individual A_miRNA/siRNAs were generated by viral infection and FACS enrichment of cells expressing green fluorescent protein (GFP), a reporter for viral infection (Liu et al., 2000). A_miRNA/siRNAs expressing cell lines were then infected with firefly Luciferase virus along with control Renilla Luciferase virus. Four days after infection, luciferase activity was measured using the luciferase assay. Firefly luciferase activity was normalized using Renilla luciferase activity.

Inducible expression of B1_C02-3 microRNA from a Polymerase II promotor. A 500 base pair B1_C02-3 microRNA gene, with predicted B1_C02-3 microRNA sequence in the center, was amplified from mouse genomic DNA. This was cloned into the TetOn inducible expression vector (Clontech). A tetracycline-inducible cell line was generated using this vector, and induced at various doxycycline concentrations. A radiolabeled probe against B1_C02-3 was used to detect the mature microRNA and unprocessed precursor, using Northern blot analysis. Ethidium staining of 5S RNA served as a loading control.

Expression of microRNAs in developmental hematopoietic organs. To determine whether microRNAs are components of the molecular machinery that regulate mouse hematopoiesis, we cloned over 100 microRNAs from mouse bone marrow and uncovered three microRNAs: miR-181, miR-223 and miR-132, that are differentially or preferentially expressed in hematopoietic tissues and are thus considered hematopoietic-specific.

Expression of microRNAs in during hematopoietic lineage commitment. To test whether microRNAs can regulate hematopoietic lineage differentiation, the effect of microRNA expression in bone marrow progenitor cells was examined. Lineage-negative bone marrow cells were isolated and infected with control retroviral construct (vector), or retroviral constructs expressing hematopoietic microRNAs, miR-30, miR-132s, or miR-181 and miR-223. All constructs contained a GFP reporter to indicate virally infected cells. Infected hematopoietic progenitor cells were seeded onto S17 stromal cells, and cultured in medium containing IL-3, IL-6, IL-7, and stem cell factor. For each infection, twelve culture replicates were conducted. Cells were fed with fresh growth medium every five days. After 10 days of culture, both suspended and adherent cells were harvested and stained with the indicated lineage markers. Virally infected cells (GFP-positive cells) were analyzed for the lineage profiles using FACS. In all cases, more than 50% of the cells were GFP positive at the time of analysis. Hematopoietic precursor cells were infected with vectors that express a control vector (no microRNA), miR-30, or the hematopoietic microRNAs, miR-181, miR-132s or miR-223. miR-30 which was cloned from bone marrow but only detectable in lung and kidney on Northern was used as negative control.

Results

1. Expression of Endogenous microRNAs

Ectopic expression of microRNAs using short miRNA hairpins. The expression of ~70 nt-microRNA hairpins (miR-132s) using the H1 expression cassette of the "double-copy" retroviral constructs compared with the "single-copy" constructs was determined using Northern blot analysis. This "double-copy" (DC) configuration, provided robust and consistent expression of the microRNA hairpin precursors. Although the transcribed microRNA hairpin precursors (band depicted with arrow in FIG. 1b) were in abundance, mature microRNA products were not detected in 293T, NIH3T3 or bone marrow cells (FIG. 1b). The reduction of the hairpins to the minimal-length miR-223 did not detectably improve the efficiency of microRNA processing (FIG. 1c). The substitution of a perfect match microRNA complementary strand miR-223-Si and miR-132s-Si also did not significantly improve the efficiency of microRNA processing (FIG. 1c.). These results demonstrated that short miRNA hairpins, while effectively transcribed in variety cell types using the double-copy expression constructs, cannot be effectively processed into mature miRNAs of endogenous forms. Changing the miRNA hairpin into a siRNA-like stem-loop (i.e., from the normally non-perfectly paired stem-loop to a perfectly paired stem-loop), did not significantly improve the miRNA processing efficiency. The resulting small RNA products, when detected are typically different from the endogenous miRNAs in their size and heterogeneity pattern (FIG. 1c). All these results suggest that additional elements, beside the hairpin itself, are required for proper miRNA expression and processing, and that additional elements might be located within a larger miRNA genes that contains the miRNA hairpin.

Expression of microRNA+Flanking Sequences.

We hypothesized that elements required for miRNA maturation might be contained in the genomic sequences flanking a predicted miRNA hairpin. To test this, we amplified miR-223 genes of different length, which contained the miR-223 minimal hairpin and the indicated length of genomic sequences flanking the predicted miRNA-223 hairpin (FIG. 2a). These gene segments were cloned into the H1 expression cassette of the double-copy MSCV constructs (FIG. 1a). Northern analysis of these miR-223 expression revealed that miR-223 genes at least 137 nucleotides long could be effectively processed into the hairpin precursor (FIG. 2b, arrow, P) and mature miR-223 (FIG. 2b, arrow, miR). The matured miR-223 RNAs have the sizes and heterogeneity pattern similar to the endogenous bone marrow miR-223 RNAs. Interestingly, the smaller miR-223 genes resulted accumulation of miR-223 gene transcripts that were not processed into the hairpin precursor and mature miR-223 (FIG. 2b).

Further analysis of the cytoplasmic (FIG. 2c) and nuclear (FIG. 2d) localization of miR-223 transcripts and processed products revealed that miRNA processing was not limited by nuclear export of miR-223 transcripts. Abundant miR-223 transcripts (miR-223-67Si to miR-223_107) were present in the cytoplasm but were not processed into miR-223 hairpin precursor and mature miRNA (FIG. 2c). This result demonstrates that the Dicer enzyme (a cytoplasmic enzyme that is partly responsible for miRNA processing) cannot directly process these longer hairpins, despite their presence in the cytoplasm. When the longer miR-223 genes were used (miR-223_137 to miR-223_500), mature miR-223 can be readily detected on the northern blot (FIG. 2b). Interestingly, a band of the size of the predicted hairpin precursor of miR-223 was also observed in these lanes (FIG. 2b, P). Furthermore, mature miR-223 and its hairpin precursor can only be seen in cytoplasm fraction, but not in the nuclear fraction. Take together, these results suggest that a pre-Dicer processing step is be required to generate the miRNA hairpin precursor that can be recognized by Dicer. The flanking sequence of miRNA hairpin gene is essential for this non-Dicer processing step.

Figure 3:
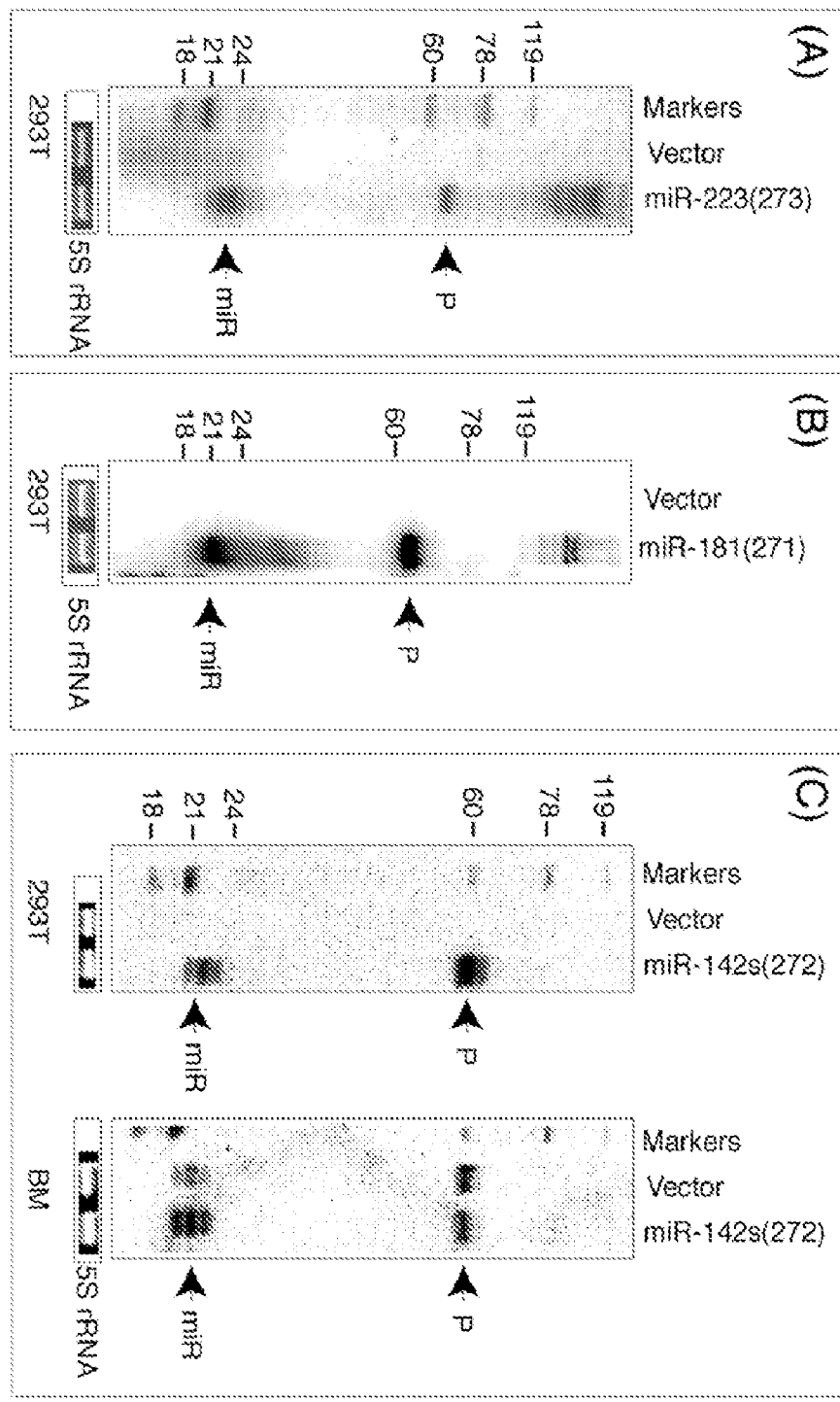
FIG. 3. Examples of miRNA expression using longer miRNA genes containing a miRNA hairpin and its correspondent flanking sequences. The longer miRNA gene is about 270 nt in length, and consists of ~20 nt miRNA sequence and 125 nt flanking sequence on both sides of the miRNA. Northern analysis of miR-223 (a), miR-181 (b), or miR-132s (c) expression from longer miRNA genes of ~270 nt in length in 293T or primary bone marrow cells.

Based on the example of miR-223 gene expression (FIG. 3), 40 nt or longer flanking sequence on one or both sides of the miR-223 hairpin precursor is required for miR-223 expression and maturation. The lower limit of the length of the flanking sequences may vary from one miRNA gene to another. Thus, to ensure the flanking sequences contain proper processing signal, we choose to express miRNA genes with 125 nt flanking sequences amplified from predicted miRNA genomic loci. Amplified miRNA genes were place into the H1 expression cassette of the double-copy retroviral construct. We were able to express miR-223, miR-181 and miR-132s (FIG. 3a-c), as well as 10 other miRNA tested (data not shown). Over-expression of a hematopoietic miRNA can also be achieved in hematopoietic progenitor cells, where the endogeneous miRNA is also present (FIG. 3c).

Figure 4:
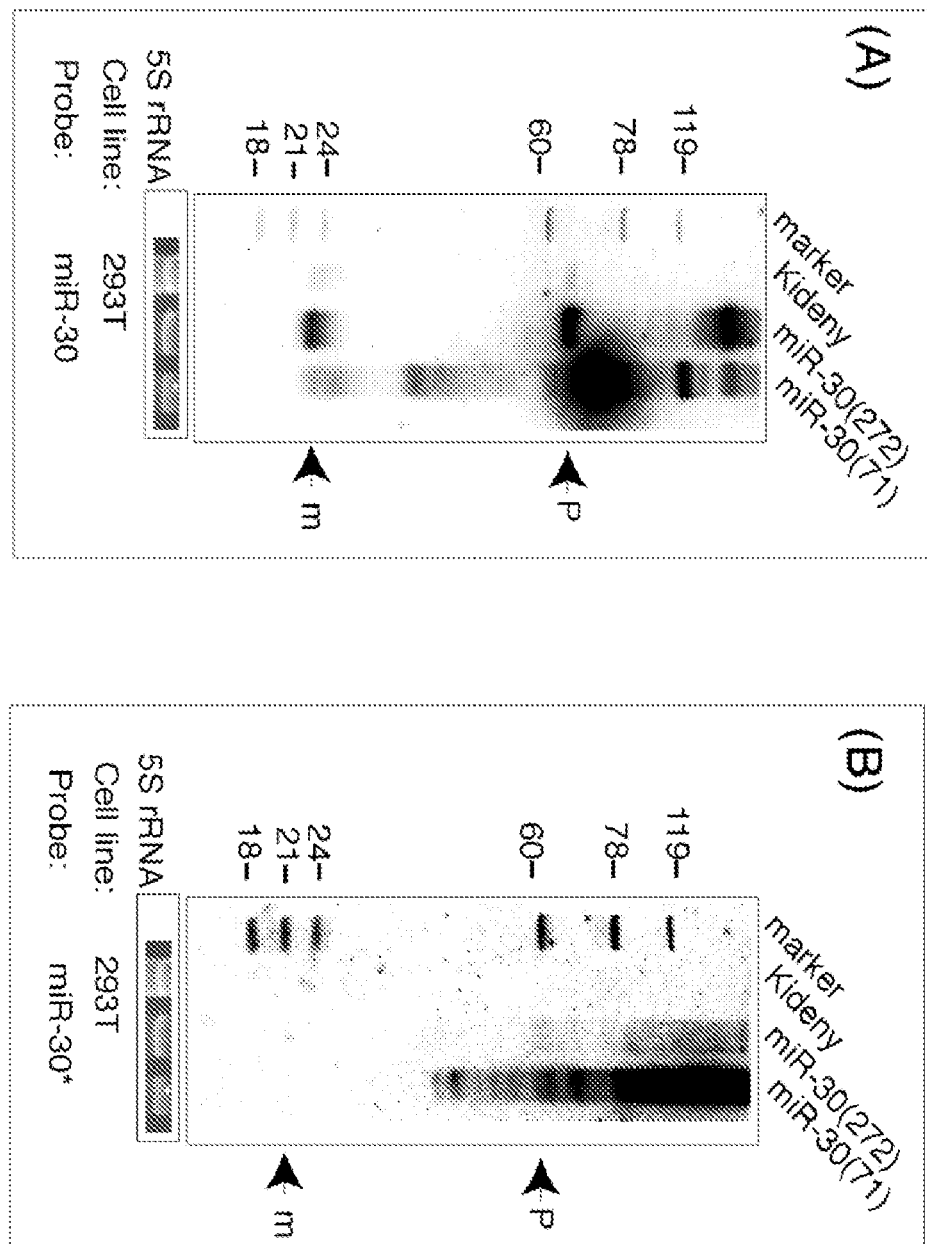
FIG. 4. Northern analysis of the expression and maturation of miR-30 from a longer precursor (272 nt) and a minimal hairpin precursor (71 nt). Northern analysis of miR-30 expression and maturation using probes against miR-30 (a), or miR-30* (b). miR-30* is the small RNA processed from the opposite arm of the miR-30 hairpin precursor.

We also compared the expression of miR-30 when expressed from a shorter hairpin (71 nt) or a longer (272 nt) miRNA gene. The longer miR-30 gene can be efficiently expressed and processed into the hairpin precursor and mature miR-30 (FIG. 4a). While trace amount of mature miR-30 is processed from a shorter hairpin (71 nt), its processing is very inefficient. Moreover, we noted that using miRNA flanking-sequence to facilitate miRNA expression not only increased miRNA processing efficient but also helped to maintain asymmetric miRNA expression. For example, only the miR-30 strand but not the miR-30* strand can be detected when miR-30 was expressed from the longer (272 nt) precursor (FIG. 4). In contrast, others have shown that both miR-30 and miR-30* strand were detected when miR-30 was expressed from a shorter hairpin precursor placed in the context of heterogenous mRNA transcripts (Zeng et al. Mol. Cell, 9:1327-1333). Maintaining asymmetrical miRNA processing may be critical for ensuring the specificity of miRNA regulation in vivo.

Ectopically Expressed miRNAs Repress Reporter Gene Expression.

A luciferase reporter system was generated for testing microRNA-mediated repression in mammalian cells (FIG. 5a). The firefly luciferase gene was fused to a mutated C. elegans lin-41 3'UTR (lin-41 3'UTR-delta) in which an 80-nt segment containing both let-7 complementary sites (green) was deleted, and replaced with a miR-223 perfect complementary site. In a control reporter, the Renilla luciferase gene was fused to the lin-41 3'UTR-delta. All luciferase genes are under the control of the viral LTR promotor. Virus was produced by transfecting the constructs into the BOSC23 viral packaging cell line and titered by infecting NIH3T3 cells. NIH3T3 cells stably expressing miR-223 or vector were infected with equal titer of fLuc-lin41UTRdelta+miR-223 target or fLuc-lin41UTRdelta−miR-223 target virus along with control virus rLuc-lin41UTRdelta. Four days after infection, luciferase activity was measured and firefly luciferase activity was normalized using Renilla reporter. The ectopically expressed miR-223 reduced by 4-fold expression of a luciferase reporter gene that had a miR-223 complementary site within its 3' UTR, confirming that the miRNA was incorporated into a miRNA ribonucleoprotein complex (miRNP) and was capable of gene silencing (FIG. 5b).

2. Expression of Artificial-microRNA/siRNAs Utilizing miRNA-Processing Signals

Figure 2:
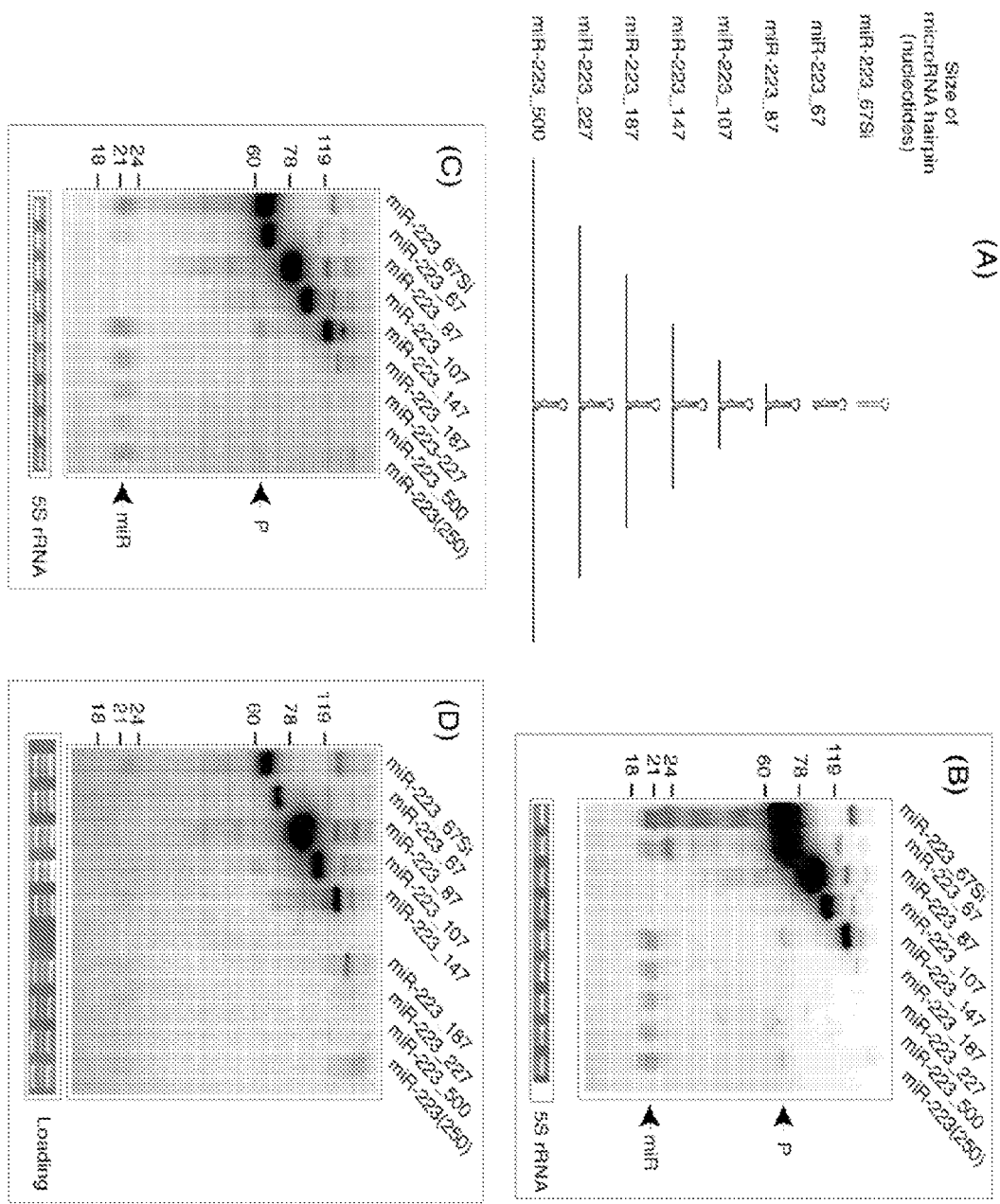
FIG. 2. (a) Schematic of miR-223 genes containing the miR-223 minimal hairpin and increasing amounts of flanking genomic sequences. miR-223_67 is the predicted 67-nucleotide hairpin that contains miR-223. miR-223_67Si is a perfect complement hairpin derived from the original bulged miR-223_67 hairpin. (b to d) Northern analysis of the expression of miR-223 genes with different length of flanking sequences in 293T cells. Total cellular RNA (b), or cytoplasmic RNA (c), or nuclear RNA (d) from 293T cells transfected with indicated miR-223 expression constructs was analyzed.

DNA vectors that express perfect complementary short hairpins RNAs are commonly used to generate functional siRNAs. However, the efficacy of gene silencing mediated by different short-hairpin derived siRNAs is inconsistent, and a substantial number of short-hairpin siRNA expression vectors can trigger an anti-viral interferon response (Nature Genetics, 2003, 34:263). Moreover, siRNA short-hairpins are typically processed symmetrically, in that both the functional siRNA strand and its complement strand are incorporated into the RISC complex. Entry of both strands into the RISC can decrease the efficiency of the desired regulation and increase the number of off-target mRNAs that are influenced. In comparison, endogenous miRNA processing and maturation is a fairly efficient process that is not expected to trigger an anti-viral interferon response. This process involves sequential steps that are specified by the information contained in miRNA hairpin and its flanking sequences (FIG. 2). Thus, we designed a novel strategy to express artificial-microRNA/siRNAs utilizing miRNA-processing signals.

Figure 6:
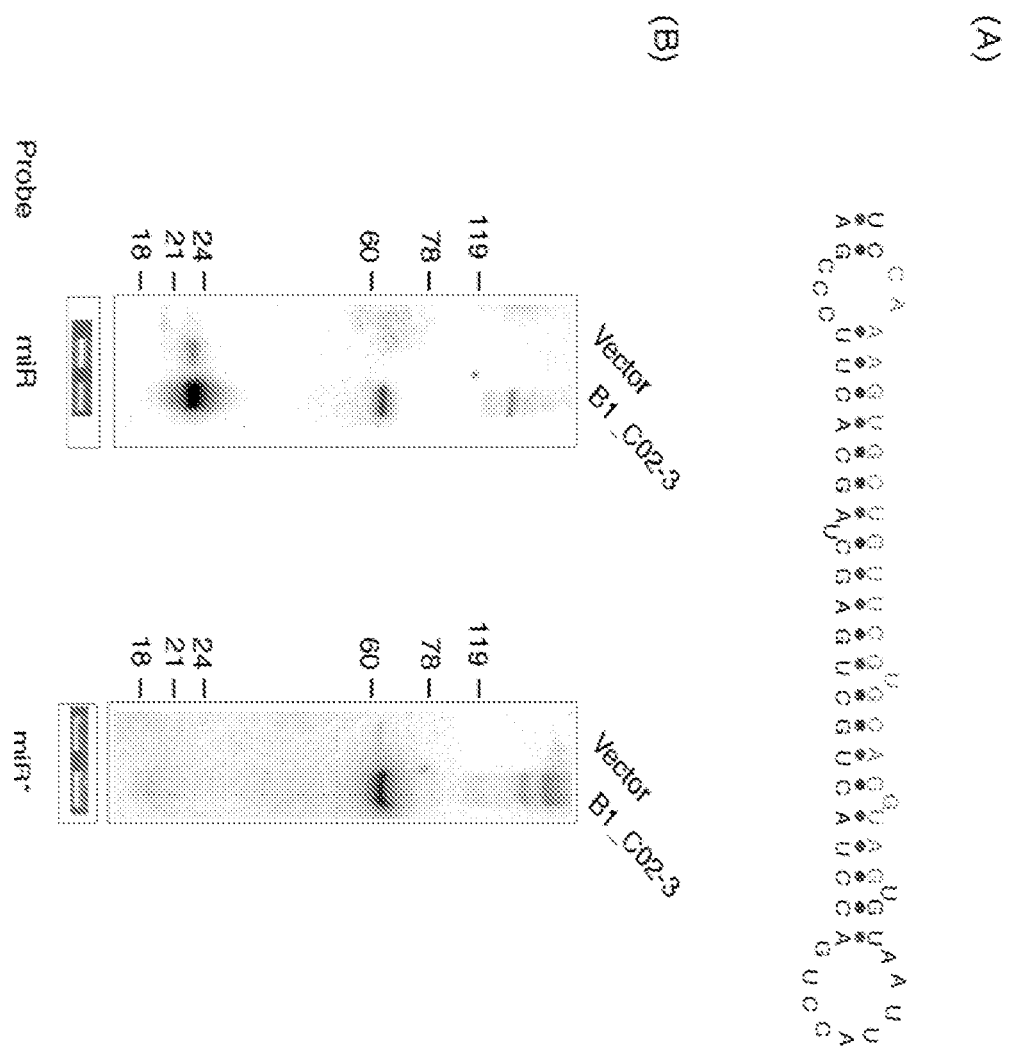
FIG. 6. (a) Schematic diagram of the predicted stem-loop structure of the B1_C02-3 miRNA (SEQ ID NO.:24). (b) Northern analysis of B1_C02-3 expression and maturation using probes against the miRNA or the miRNA*.

To this end, we selected the B1_C02-3 miRNA as a template for artificial-microRNA/siRNA expression (FIG. 6). Shown in FIG. 6a are the predicted stem-loop structure of B1_C02-3 miRNA and the actual sequence of B1_C02-3 miRNA (Green letters). Based on cloning analysis, all B1_C02-3 clones are 23 nt in length, and no miR* strand was found in cloning, while B1_C—$O_2$-3 was cloned over 18 times. Consistent with cloning analysis, northern analysis of ectopically expressed B1_C02-3 revealed that the expressed miRNA was asymmetrically processed into a defined length (FIG. 6b). In comparison, many miRNAs are processed into different lengths with heterogeneity mostly seen in the 3' end; a few miRNAs are also not asymmetrically processed in that both miR and miR* strands can be found at similar frequency. Thus, we hypothesized that the information for specific B1_C02-3 processing is defined by its stem-loop and flanking sequences, and this information can be utilized to express artificial-microRNA/SiRNA with defined length and asymmetrical strand accumulation.

Based on this hypothesis we designed the following strategy to express artificial-microRNA/siRNAs utilizing B1_C02-3 templates (FIG. 7). In brief, a B1_C02-3 gene of about 273 nt in length containing the miRNA and 125 nt flanking sequences on each side of the miRNA was cloned into the double-copy retroviral expression constructs. This construct can effectively express B1_C02-3 (FIG. 6b). A XhoI restriction enzyme site was introduced into the B1_C02-3 hairpin flanking sequence. This allowed us to easily replace the B1_C02-3 miRNA hairpin with an artificial-microRNA/siRNA hairpin. Some features of the B1_C02-3 miRNA hairpin structure, the loop and buldges (indicated with arrows in FIG. 7) surrounding the miRNA stem, were preserved in all artificial-microRNA/siRNA hairpins. These features might be important to determine the boundary of miRNA processing. A stem formed by an artificial-microRNA/siRNA sequence (with a length of 19 to 23 nt) and its perfect complement strand replaced the B1_C02-3 miRNA stem. Expression of the artificial-microRNA/siRNA and B1_C02-3 chimeric gene should produce an asymmetric artificial-microRNA/SiRNA sequence with "CA" on its 5'end (FIG. 7). Because the expression and processing of artificialmicroRNA/SiRNA utilizes the miRNA processing machinery, the final artificial-microRNA/SiRNA products should be effectively incorporated into the functional miRNP/RISC.

Figure 8:
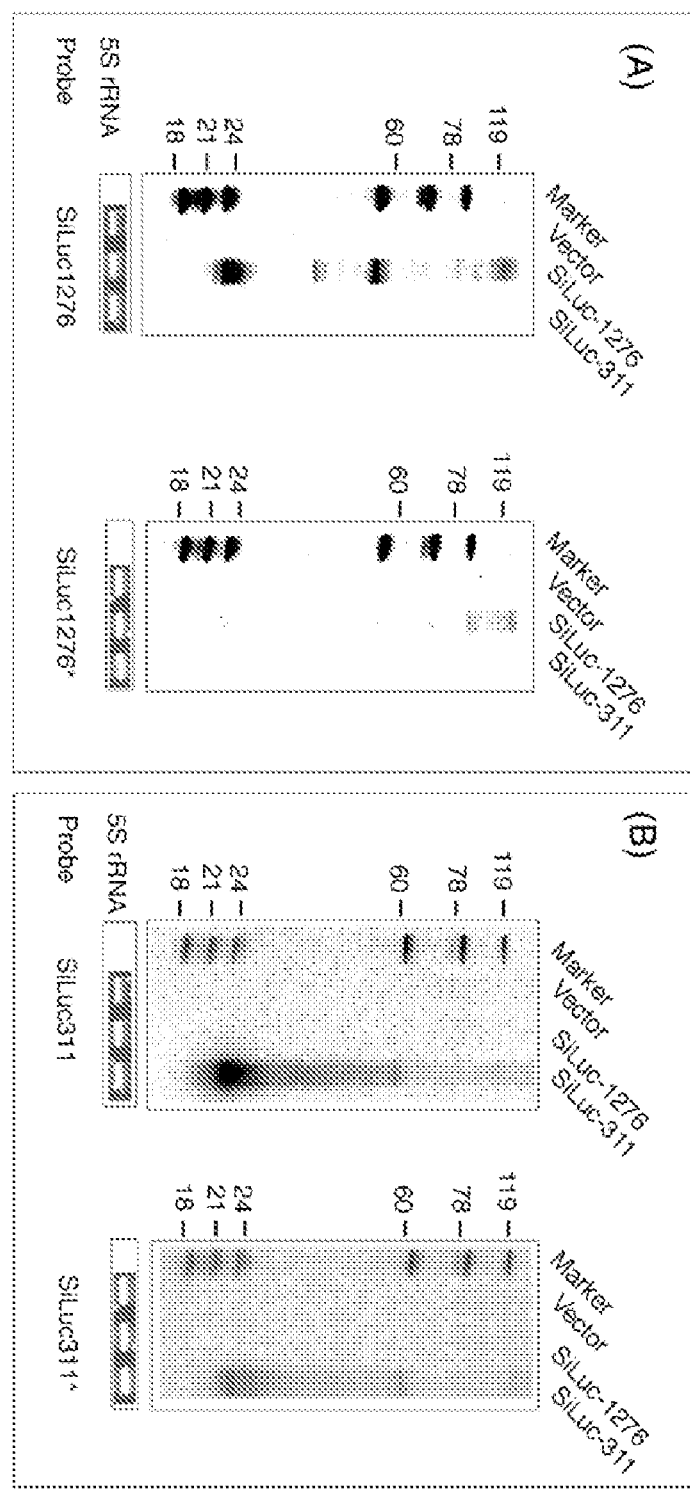
FIG. 8 Expression of artificial-microRNA/siRNAs using a microRNA template. (a) Northern analysis of ectopically expressed SiLuc-1276 and SiLuc-1276*. (b) Northern analysis of ectopically expressed SiLuc-311 and SiLuc-311*.

To test this design, artificial-miRNAs/SiRNAs were designed to target 21-nucleotide unique sequences in the firefly luciferase gene. Northern blot analyses (FIG. 8), using probes against sense and antisense strands of the artificial-miRNAs/siRNAs, were used to determine the expression and processing of SiLuc-1276 and SiLuc-311. In both cases, we observed asymmetrically processed SiLuc-1276 and SiLuc-311 products of 23 nt in length. These results demonstrate that our design properly preserved processing information for B1_C02-3, and can be used to express virtually any desired artificial-miRNAs/siRNAs.

Figure 9:
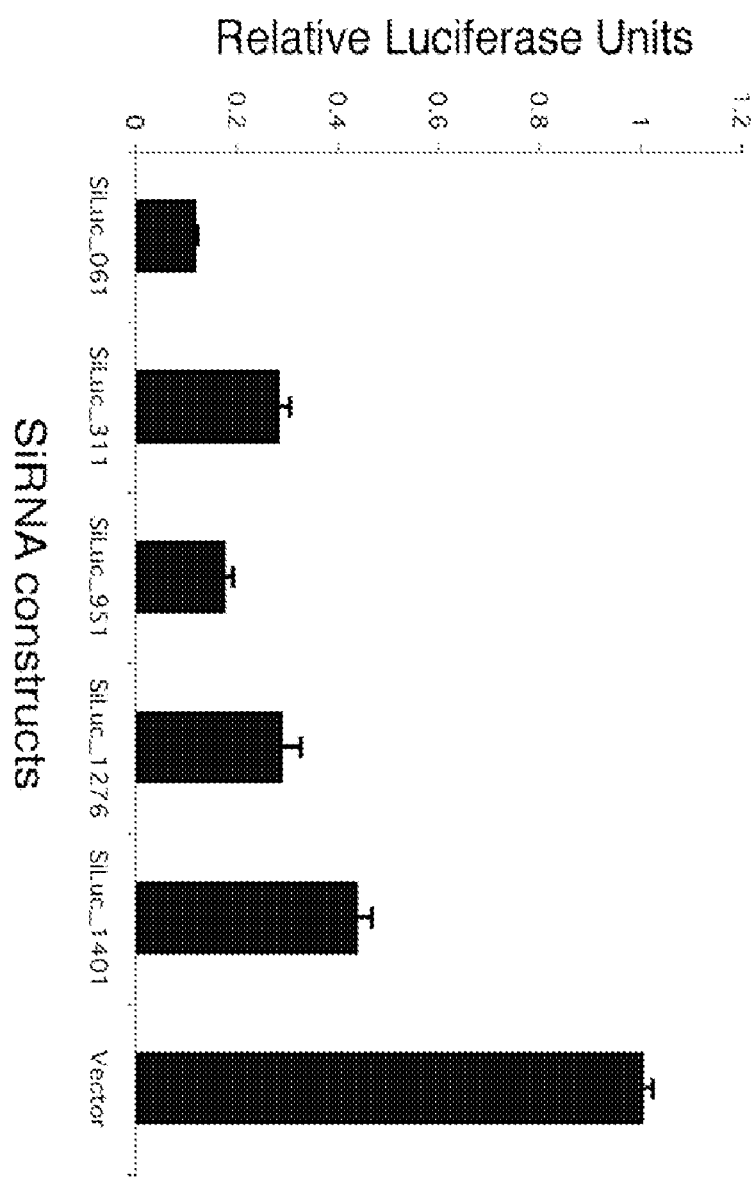
FIG. 9 Repression of reporter gene expression by ectopically expressed artificial-microRNA/SiRNAs.

We analyzed the function of ectopically expressed artificial-miRNAs/siRNAs in their ability to mediate gene silencing. A series of artificial-miRNAs/SiRNAs expression constructs were designed to target a luciferase reporter gene. NIH3T3 cells stably expressing artificial-miRNAs/siRNAs or vector were infected with the firefly Luciferase reporter along with a control Renilla reporter. Four days after infection, luciferase activity was measured and firefly luciferase activity was normalized using the Renilla reporter. The ectopically expressed artificial-miRNAs/siRNAs against Luciferase can specifically reduce firefly luciferase activity up to 90%. Four out of five constructs could reduce reporter expression by at least 60%. These results confirm that the expressed artificial-miRNAs/SiRNAs was incorporated into a miRNA ribonucleoprotein complex (miRNP/RISC) and was capable of gene silencing (FIG. 9).

3. Expression of miRNAs Using Different Promoters

Figure 10:
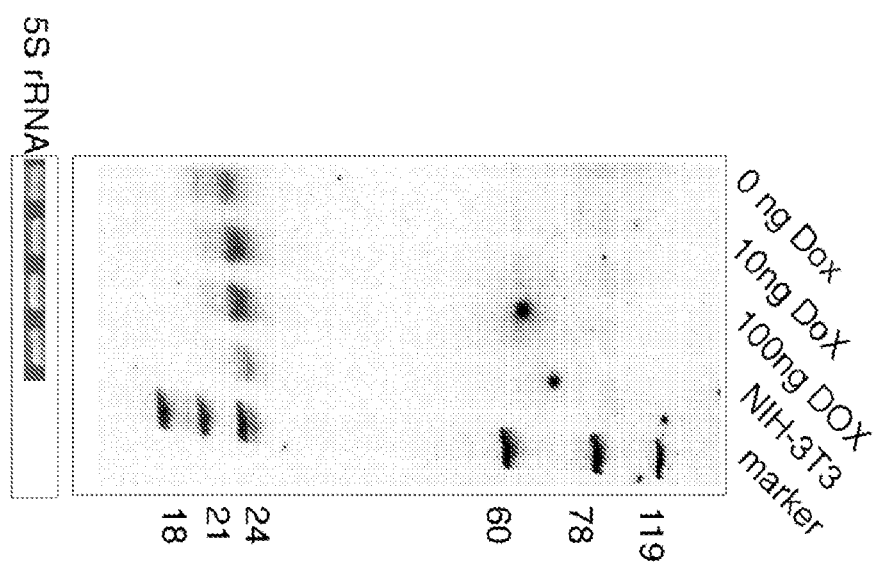
FIG. 10. Inducible expression of B1_C02-3 microRNA at various concentrations of Doxycycline.

Expression of microRNAs from Pol II and Pol III promoters. One strategy to express the miRNA is to include a sufficiently large DNA fragment such that the miRNA is expressed under the control of its native promoter. A second strategy is to use heterologous promoters. We have demonstrated that a microRNA can be effectively expressed and processed from a microRNA transcript containing the microRNA and corresponding genomic flanking sequences using a pol III expression cassette. In FIG. 10 we also show that pol II heterologous promoters can be used.

Inducible expression of microRNA using the TetOn system. (FIG. 10) One strategy to express the miRNA is to include a sufficiently large DNA fragment such that the miRNA is expressed under the control of its native promoter. A second strategy is to use heterologous promoters. We have demonstrated that a microRNA can be effectively expressed and processed from a microRNA transcript containing the microRNA and corresponding genomic flanking sequences using a pol III expression cassette. In FIG. 10 we also show that pol II heterologous promoters can be used. Such promoters include those that are used in available mammalian expression systems including tissue-specific promoters and inducible promoters. TetOn system is a commercial inducible expression system from Clontech Inc. This is of particular interest because current siRNA expression systems utilize pol III promoters, which are difficult to adapt for inducible expression. In FIG. 10, we showed the expression of miRNA (B1_C02-3) using the Clontech TetOn expression system. A B1_C02-3 gene with 500 nt flanking sequence was cloned into the pRev-TRE vector. This construct was then packaged into retrovirus and used to infect a Tet-On cell line expressing the reverse tetracycline-controlled transactivator (rtTA). B1_C02-3 is inducibly expressed in response to varying concentrations of the teratcycline derivate doxycycline (Dox). Similarly, this system can be used for expression of artificial microRNAs.

4. miRNAs Modulate Hematopoietic Lineage Differentiation

Figure 11:
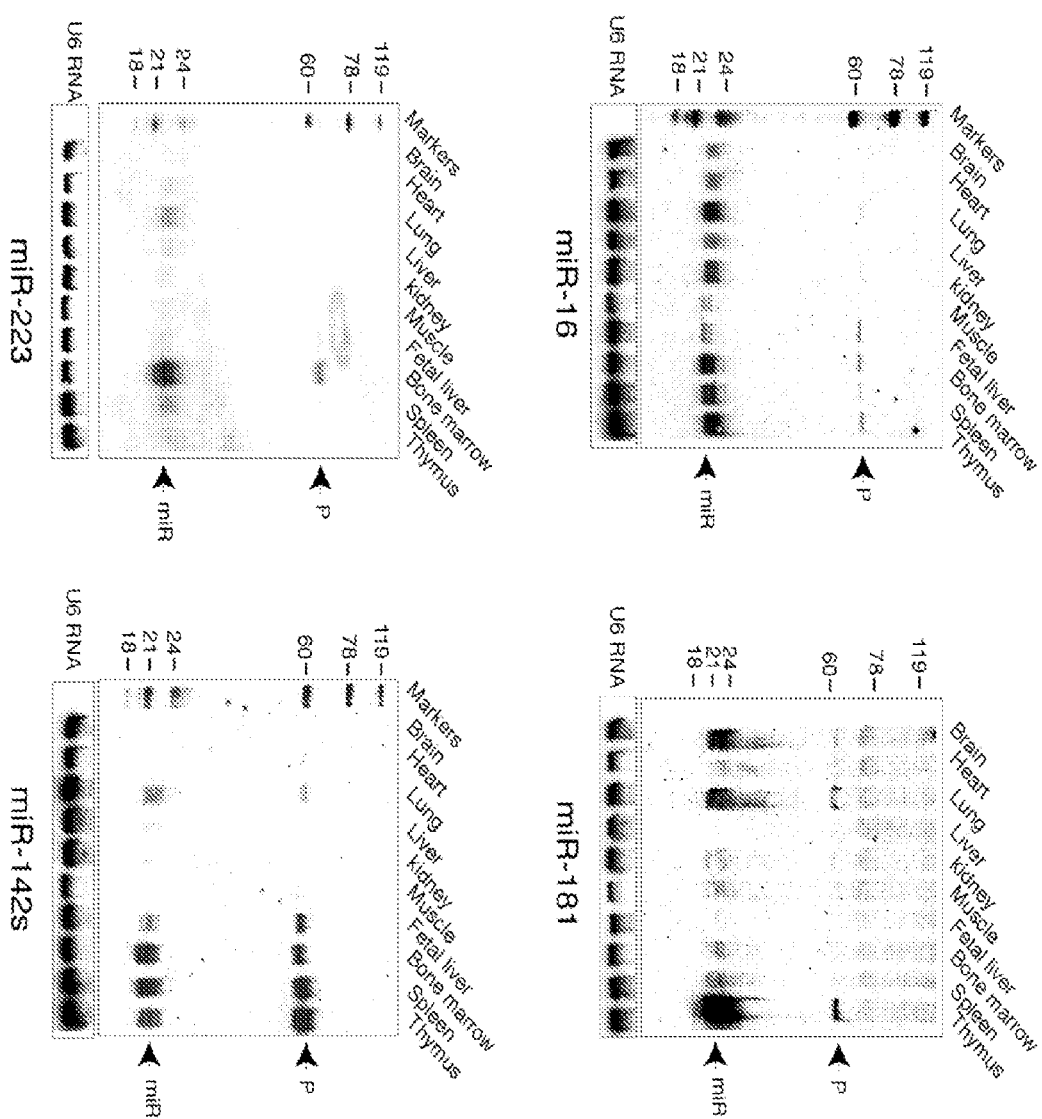
FIG. 11. Tissue and developmental expression of microRNAs cloned from mouse bone marrow. Northern analyses were used to determine microRNA expression in different mouse tissues, including brain, heart, lung, liver, kidney, muscle, fetal liver, bone marrow, spleen, and thymus.

Expression of microRNAs in hematopoietic tissues. To investigate whether microRNAs play a role in mammalian development and in particular might regulate mammalian hematopoiesis, we cloned more than 70 unique microRNAs from mouse bone marrow. miR-132s, the microRNA found at a breakpoint of a t(8:17) translocation associated with an aggressive B-cell leukemia (Gauwerky et al., 1989, Proc. Natl. Acad. Sci. USA, 86:8867-8871), was expressed in all four hematopoietic tissues tested: fetal liver, and adult bone marrow, spleen, and thymus, with little or no expression in the non-hematopoietic tissues. The lung was the only other tissue with appreciable miR-132s expression (FIG. 11). Expression in E13 fetal liver suggested that miR-132s might function in early hematopoietic development. Expression of mature miR-132s was highest in thymus, the primary lymphoid organ that mainly contains T-lymphocytes. Expression was much lower in bone marrow, which consists of hematopoietic stem cells and myeloid, erythroid and lymphoid cells at a variety of differentiation stages, and spleen. Interestingly, accumulation of the presumed miR-132 precursor (~60 nt band, FIG. 11) was high and the ratio of mature to precursor 21 nt RNAs varied in different tissues, suggesting post transcriptional regulation of microRNA expression at the level of precursor processing or RNA stability.

miR-223 was very strongly expressed in bone marrow and was detectable in spleen but essentially absent in E13 fetal liver, thymus, and all other adult mouse tissues tested (FIG. 11). miR-181 was very strongly expressed in thymus and was detectable in bone marrow and spleen but essentially negative in E13 fetal liver and all other mouse tissues tested except for high expression in brain and lung. miR-181 and miR-223 expression in fetal liver was barely detectable, suggesting that they only function in adult hematopoiesis. Thus miR-181, miR-223 and miR-132s are differentially expressed in hematopoietic tissues and their expression is regulated during development.

microRNAs are Regulated in Hematopoietic Lineage Commitment.

Figure 12:
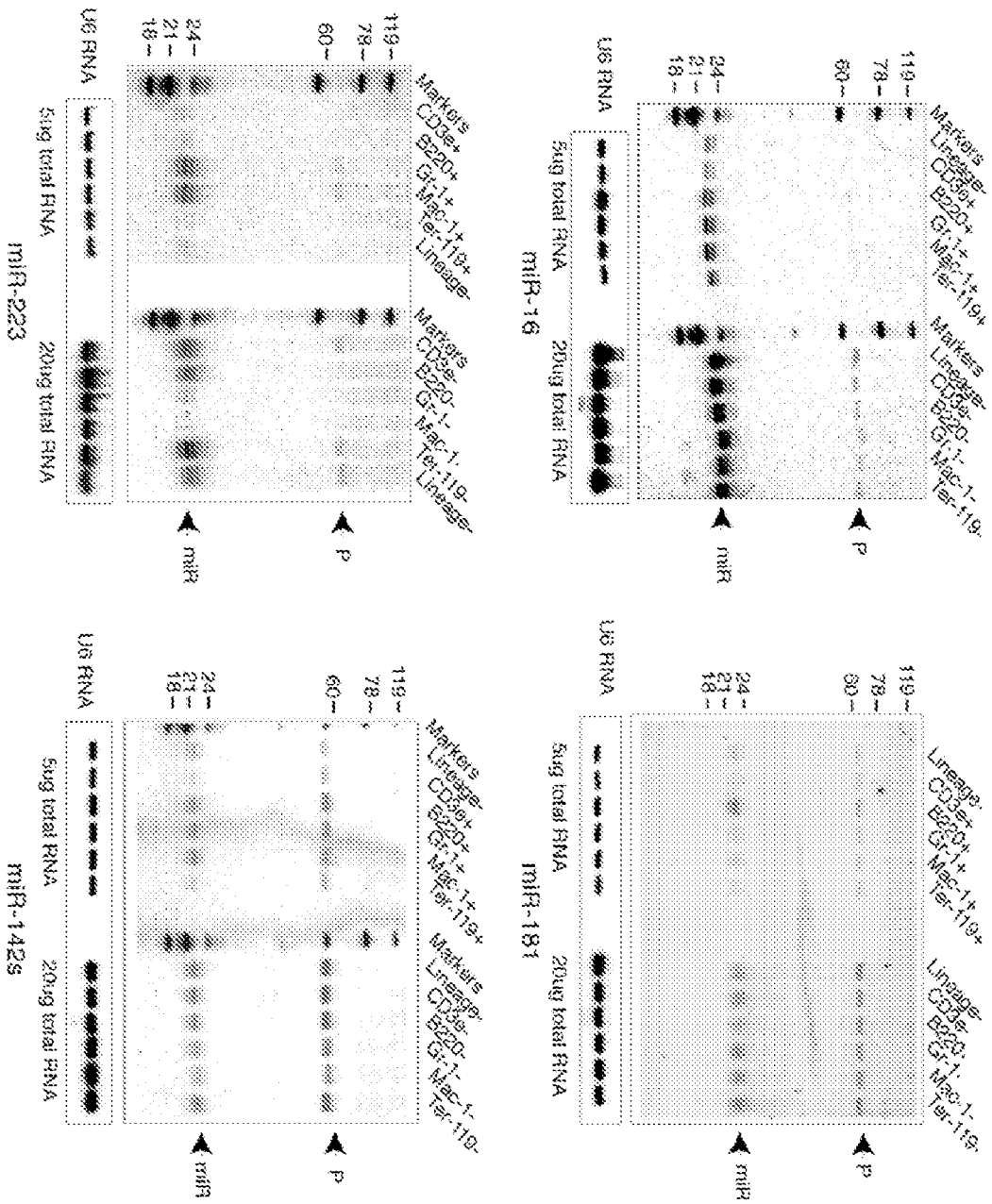
FIG. 12. Northern blot showing microRNA expression during hematopoietic lineage commitment.

Because bone marrow, spleen, and thymus, each have specialized functions in adult hematopoiesis and comprise significantly different cell types, the differential expression of the miRNAs in these complex tissues suggested that individual hematopoietic cell types might differentially express the miRNAs. Indeed, when cells within bone marrow were sorted based on lineage markers, they were found to differentially express the hematopoietic miRNAs (FIG. 12). In contrast, expression of miR-16, an miRNA seen in a broad range of tissues, was more constant.

Mature miR-181 expression in the bone marrow cells was detectable in undifferentiated progenitor cells (Lin$^-$) and up-regulated in the differentiated B-lymphocytes, marked by the B220 surface antigen. In other differentiated lineages, miR-181 expression did not increase over that seen in Lin$^-$ cells. Note that sorted lineage cell populations are about 85% pure, thus some residual miRNA signal in the other lineages might be caused by contamination of B220$^+$ cells. Expression of the miR-181 precursor was at similar levels in all lineages, suggesting that the differential accumulation of the mature miR-181 during hematopoietic lineage commitment might be regulated at the level of miRNA processing or the rate of turnover.

miR-223 expression was confined to myeloid lineages (Gr-1$^+$ and Mac-1$^+$) with barely detectable expression in T- and B-lymphoid and erythroid lineages (CD3e$^+$, B220$^+$, and Ter119$^+$, respectively; FIG. 12). This observation is consistent with miR-223 expression in bone marrow but not spleen and thymus (FIG. 11). miR-132s expression was lowest in the erythroid lineage (Ter-119+) and highest in myeloid lineages (Gr-1+ and Mac-1+), consistent with its ubiquitous expression in bone, spleen and thymus (FIGS. 11 and 12).

For each of the miRNAs, specific expression was validated by the reduction of correspondent miRNA expression in the reciprocal lineage-depleted cell populations (FIG. 12, right panels). In addition, expression of all four miRNAs was low in Lin− cells relative to their preferred Lin+ cell populations, suggesting that these miRNAs were induced upon lineage commitment and differentiation.

microRNAs are Capable of Modulating Hematopoietic Lineage Commitment.

Figure 13:
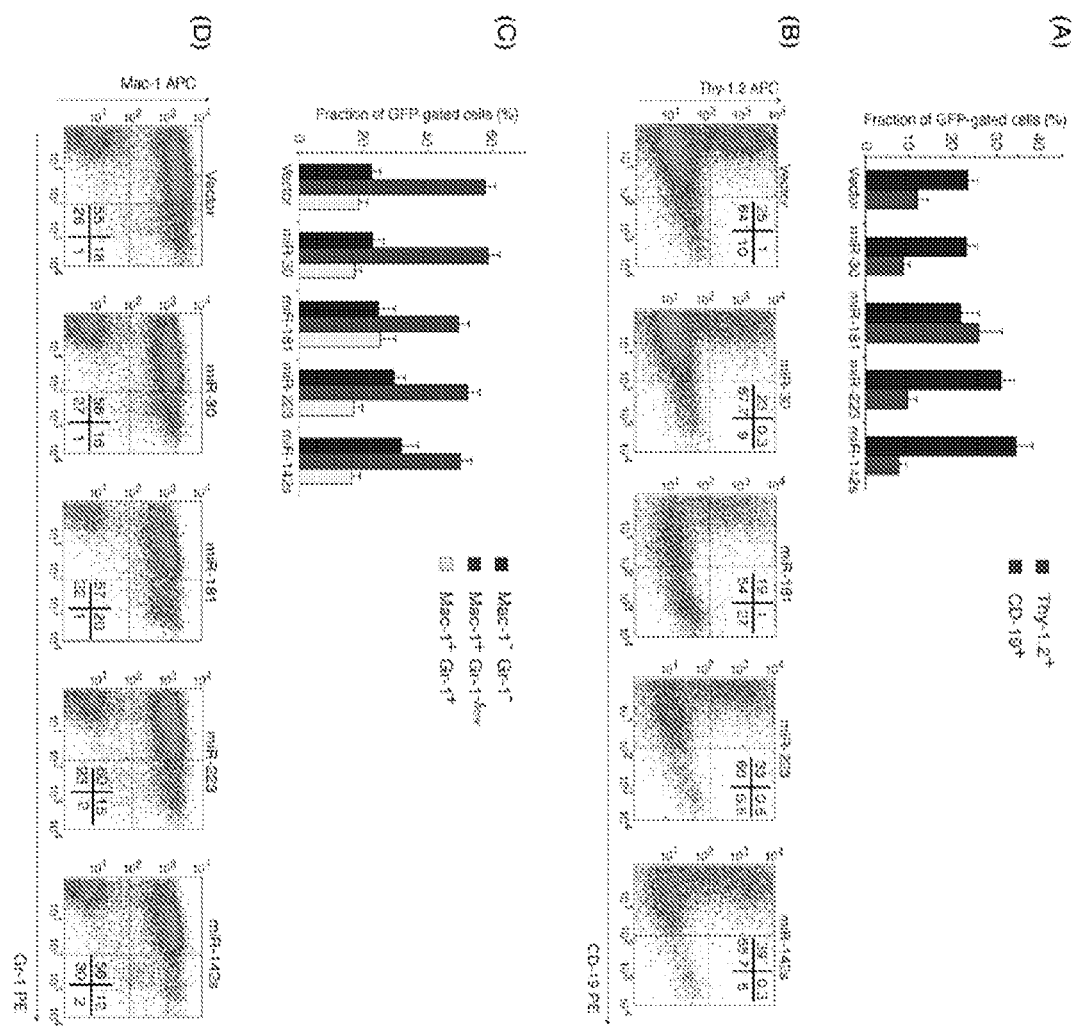
FIG. 13. (a) Graph to show percentage Thy1.2 positive (Thy1.2$^+$) cells and CD-19 positive (CD-19$^+$) cells among the differentiating hematopoietic progenitor cells ectopically expressing no microRNA (vector), a non-hematopoietic microRNA (miR-30), or either of three hematopoietic microRNAs (miR-223, miR-132, or miR-181). (b) Representative FACS analyses of Thy-1.2 (Thy-1.2 APC) and CD-19 (CD-19 PE) lineage marker expression. (c) Graph to show percentage Mac-1 and Gr-1 negative cells (Mac-1$^-$ Gr-1$^-$), Mac-1 positive and Gr-1 negative to intermediate (Mac-1$^+$ Gr-1$^{-/low}$), Mac-1 and Gr-1 positive (Mac-1$^+$ Gr-1$^+$) cells among the differentiating hematopoietic progenitor cells ectopically expressing no microRNA (vector), miR-223, miR-30, miR-132, or miR-181. The average of 12 culture replicates for each construct is shown, with error bars indicating the standard deviation. (d) Representative FACS analyses of Mac-1 (Mac-1 APC) and Gr-1 (Gr-1 PE) lineage marker expression.

Hematopoietic progenitor cells from mouse bone marrow were infected with the viral vectors expressing either miR-181, miR-223, miR-132s, or a control miRNA, miR-30. Interestingly, ectopic expression of each of these microRNAs in hematopoietic bone marrow Lin− progenitor cells have differential effects on the differentiation of bone marrow progenitor cells, particularly the differentiation of T- or B-lymphoid lineages, which are indicated by the expression of Thy-1.2 or CD-19 cell surface antigens (FIG. 13).

About 23±2.5% (n=12) or 12±2.3% (n=12) differentiated cells expressed Thy-1.2 or CD-19 antigen, respectively, when infected with control vector. Over-expression of miR-30 did not significantly alter the ratio of T- and B-lymphoid lineage cells, in that the marker expression was essentially unchanged compared to that of cells infected with the empty vector. This indicated that merely expressing an arbitrary microRNA did not markedly influence lymphoid differentiation. In contrast, about 21±4.2% (n=12) or 26±1.7% (n=12) differentiated cells expressed Thy-1.2 or CD-19 antigen, respectively, when infected with miR-181 expression virus. Thus, expression of miR-181 substantially affected the lineage differentiation, resulting in more than a 2-fold increase in B-lymphoid lineage with little change in T-lymphoid lineage. In contrast, ectopic expression of miR-132s and miR-223 resulted in opposite effects, with a 30~40% increase in the T-lymphoid lineage and a slight reduction in the B-lymphoid lineage, and more significant change in the ratio of T/B-lineage cells which increased from ~2-fold (vector) to 2.5 (miR-223) or 4.5-fold (miR-132s), respectively.

Modest effects were seen when analyzing these cells for myeloid lineage markers (FIGS. 13c and d). Neutrophils are Mac-1 and Gr-1 double-positive cells (Mac-1+ Gr-1+), whereas monocytes are Mac-1 positive and Gr-1 negative-to-low (Mac-1+ Gr-1−/low). Non-myeloid cells were Mac-1 and Gr-1 double-negative (Mac-1− Gr-1−); they mostly expressed Thy-1.2 or CD-19 lymphoid markers. Overexpression of the control miR-30 had little if any effect on Mac-1 and Gr-1 expression. Over-expression of either miR-132s or miR-181 led to a small decrease in Mac-1+ Gr-1−/low cells but expression of miR-181 led to a noticeable increase in Mac-1+ Gr-1+ cells.

The demonstration that certain miRNAs are differentially expressed in hematopoietic lineages in vivo and are able to alter lineage commitment in vitro provides solid evidence that microRNAs represent a class of molecules that regulate mammalian development. This supports the notion that the roles of translational regulation in hematopoiesis and, more broadly, vertebrate development might have been under-appreciated. Furthermore, modulating the expression of miRNAs can have therapeutic utility.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A precursor microRNA molecule, comprising:
an isolated nucleic acid comprising:
a stem-loop structure, wherein a microRNA sequence is incorporated into a stem of the stem-loop structure, and
a microRNA flanking sequence flanking each end of the stem-loop structure,
wherein each microRNA flanking sequence comprises the sequence of a naturally occurring microRNA flanking sequence at least 40 nucleotides long, wherein the naturally occurring microRNA flanking sequence comprises at least 40 nucleotides of genomic sequence that, when present within a genome, is directly adjacent to the genomic sequence of a naturally occurring microRNA-containing stem-loop structure, and wherein the microRNA sequence and the microRNA flanking sequences are not derived from the same microRNA gene.

2. The precursor microRNA molecule of claim 1, wherein each microRNA flanking sequence is between 40 and 2,000 nucleotides in length.

3. The precursor microRNA molecule of claim 1, wherein the microRNA sequence is an artificial microRNA sequence.

4. The precursor microRNA molecule of claim 1, wherein the precursor microRNA molecule includes at least two stem-loop structures.

5. The precursor microRNA molecule of claim 1, wherein the molecule has the following nucleic acid sequence

SEQ ID NO: 23

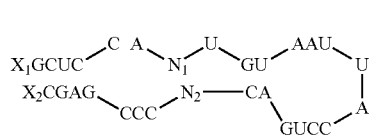

wherein $X_1$ and $X_2$ are nucleotides and wherein $N_1$ and $N_2$ are nucleic acids of 16-28 nucleotides in length and wherein $N_1$ and $N_2$ have at least partial complementarity.

6. The precursor microRNA molecule of claim 5, wherein $X_1$ and $X_2$ are each between 40 and 4,000 nucleotides in length.

7. The precursor microRNA molecule of claim 1, wherein each microRNA flanking sequence comprises at least 60 nucleotides of a naturally occurring microRNA flanking sequence.

8. The precursor microRNA molecule of claim 1, wherein each microRNA flanking sequence is between 40 and 150 nucleotides in length.

9. The precursor microRNA molecule of claim 1, wherein each microRNA flanking sequence is between 40 and 270 nucleotides in length.

10. A precursor microRNA molecule, comprising:
nucleic acid comprising:
a stem-loop structure, wherein a microRNA sequence is incorporated into a stem of the stem-loop structure, and,
a microRNA flanking sequence flanking each end of the stem-loop structure,
wherein the microRNA sequence and the microRNA flanking sequences are not derived from the same microRNA gene, and wherein each microRNA flanking sequence comprises the sequence of a naturally occurring microRNA flanking sequence at least 40 nucleotides long, wherein the naturally occurring microRNA flanking sequence comprises at least 40 nucleotides of genomic sequence that, when present within a genome is directly adjacent to the genomic sequence of a naturally occurring microRNA-containing stem-loop structure.

11. The precursor microRNA molecule of claim 10, wherein each microRNA flanking sequence is between 40 and 2,000 nucleotides in length.

12. The precursor microRNA molecule of claim 10, wherein each microRNA flanking sequence is between 40 and 4,000 nucleotides in length.

13. The precursor microRNA molecule of claim 10, wherein each microRNA flanking sequence is between 40 and 150 nucleotides in length.

14. The precursor microRNA molecule of claim 10, wherein each microRNA flanking sequence is between 40 and 270 nucleotides in length.

15. A vector for producing a precursor microRNA, wherein the vector includes (i) a sequence encoding a precursor microRNA, including a microRNA sequence incorporated into a stem of a stem-loop structure and a microRNA flanking sequence flanking each end of the stem-loop structure, and (ii) at least one promoter element, wherein each microRNA flanking sequence comprises a naturally occurring microRNA flanking sequence at least 40 nucleotides long, wherein the naturally occurring microRNA flanking sequence comprises at least 40 nucleotides of genomic sequence that, when present within a genome, is directly adjacent to the genomic sequence of a naturally occurring microRNA-containing stem-loop structure.

16. The vector of claim 15, wherein the vector is a viral vector.

17. The vector of claim 16, wherein the viral vector is a retroviral vector.

18. The vector of claim 15, wherein the at least one promoter is an inducible promoter.

19. The vector of claim 15, wherein the precursor microRNA molecule is a precursor microRNA molecule comprising a nucleic acid comprising:
a stem-loop structure, wherein a microRNA sequence is incorporated into a stem of the stem-loop structure, and, a microRNA flanking sequence flanking each end of the stem-loop structure, wherein the microRNA sequence and the microRNA flanking sequences are not derived from the same microRNA gene, wherein each microRNA flanking sequence comprises the sequence of a naturally occurring microRNA flanking sequence at least 40 nucleotides long, and wherein the naturally occurring microRNA flanking sequence comprises at least 40 nucleotides of genomic sequence that, when present within a genome is directly adjacent to the genomic sequence of a naturally occurring microRNA-containing stem-loop structure.

20. The vector of claim 15, wherein the vector has the nucleic acid sequence of SEQ ID NO. 1 or a variant thereof, wherein the variant has at least 90% identity with SEQ ID NO: 1.

21. The vector of claim 20, wherein the vector has the nucleic acid sequence of SEQ ID NO. 1.

22. The vector of claim 15, wherein the promoter is functional in mammalian cells.

23. The vector of claim 15, wherein each microRNA flanking sequence comprises a naturally occurring microRNA flanking sequence at least 60 nucleotides long.

24. The vector of claim 15, wherein the microRNA sequence is a mammalian sequence.

25. The vector of claim 15, wherein the precursor microRNA is identical to a naturally occurring stem-loop sequence which is a mammalian sequence.

26. The vector of claim 15, wherein each naturally occurring microRNA flanking sequence is a mammalian sequence.

27. The vector of claim 15, wherein the microRNA sequence is a human sequence.

28. The vector of claim 15, wherein the precursor microRNA is identical to a naturally occurring stem-loop sequence which is a human sequence.

29. The vector of claim 15, wherein each naturally occurring microRNA flanking sequence is a human sequence.

30. The vector of claim 15, wherein the promoter is a mammalian RNA polymerase II promoter.

31. The vector of claim 15, wherein the microRNA sequence and the microRNA flanking sequences are not derived from the same microRNA gene.

32. The vector of claim 15, wherein the microRNA sequence is an artificial microRNA sequence.

33. The vector of claim 15, wherein each microRNA flanking sequence is between 40 and 150 nucleotides in length.

34. The vector of claim 15, wherein each microRNA flanking sequence is between 40 and 270 nucleotides in length.

35. A host cell transfected with the vector of claim 15.

36. A vector for producing a precursor microRNA, wherein the vector includes a sequence encoding a precursor microRNA, wherein the precursor microRNA includes a microRNA sequence incorporated into a stem of a stem-loop structure and a microRNA flanking sequence at least 40 nucleotides long flanking each end of the stem-loop structure, wherein each microRNA flanking sequence comprises at least 40 nucleotides of genomic sequence that, when present within a genome, is directly adjacent to the genomic sequence of a naturally occurring microRNA-containing stem-loop structure, and wherein the microRNA sequence and the microRNA flanking sequences are not derived from the same microRNA gene.

\* \* \* \* \*

SEQUENCE LISTING

```
<160> NUMBER OF SEQ ID NOS: 28

<210> SEQ ID NO 1
<211> LENGTH: 6963
<212> TYPE: DNA
<213> ORGANISM: Artificial Sequence
<220> FEATURE:
<223> OTHER INFORMATION: Synthetic oligonucleotide

<400> SEQUENCE: 1
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcactcgg cgcgccagtc ctccgataga ctgcgtcgcc cgggtacccg tattcccaat     420
aaagcctctt gctgtttgca tccgaatcgt ggactcgctg atccttggga gggtctcctc     480
agattgattg actgcccacc tcggggggtct ttcatttgga ggttccaccg agatttggag     540
acccctgcct agggaccacc gaccccccg ccgggaggta agctggccag cggtcgtttc      600
gtgtctgtct ctgtctttgt gcgtgtttgt gccggcatct aatgtttgcg cctgcgtctg     660
```

```
tactagttag ctaactagct ctgtatctgg cggacccgtg gtggaactga cgagttctga    720
acacccggcc gcaaccctgg gagacgtccc agggactttg ggggccgttt ttgtggcccg    780
acctgaggaa gggagtcgat gtggaatccg accccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactcccct aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtccctac atcgtgacct gggaagcctt ggcttttgac   1260
cccctccct gggtcaagcc ctttgtacac cctaagcctc cgcctcctct tcctccatcc   1320
gccccgtctc tcccccttga acctcctcgt tcgacccccgc ctcgatcctc cctttatcca   1380
gccctcactc cttctctagg cgccggaatt agatcttata tggggcaccc ccgcccctta   1440
taaacttccc tgaccctgac atgacaagag ttactaacag cccctctctc caagctcact   1500
tacaggctct ctacttagtc cagcacgaag tctggagacc tctggcggca gcctaccaag   1560
aacaactgga ccgaccggtg gtacctcacc cttaccgagt cggcgacaca gtgtgggtcc   1620
gccgacacca gactaagaac ctagaacctc gctggaaagg accttacaca gtcctgctga   1680
ccacccccac cgccctcaaa gtagacggca tcgcagcttg gatacacgcc gcccacgtga   1740
aggctgccga ccccggggt ggaccatcct ctagactgcc ggatcaattc ctaccgggta   1800
ggggaggcgc ttttcccaag gcagtctgga gcatgcgctt tagcggcccc gctgggcact   1860
tggcgctaca caagtggcct ctggcctcgc acacattcca catccaccgg taggcgccaa   1920
ccggctccgt tctttggtgg cccttcgcg ccaccttcta ctcctcccct agtcaggaag   1980
ttcccccccg ccccgcagct cgcgtcgtgc aggacgtgac aaatggaagt agcacgtctc   2040
actagtctcg tgcagatgga cagcaccgct gagcaatgga agcgggtagg cctttggggc   2100
agcggccaat agcagctttg gctccttcgc tttctgggct cagaggctgg aaggggtgg   2160
gtccggggc gggctcaggg gcgggctcag gggcggggcg ggcgcccgaa ggtcctccgg   2220
aggcccggca ttctgcacgc ttcaaaagcg cacgtctgcc gcgctgttct cctcttcctc   2280
atctccgggc ctttcgacct gcaccatggt gagcaagggc gaggagctgt tcaccgggt   2340
ggtgcccatc ctggtcgagc tggacggcga cgtaaacggc cacaagttca gcgtgtccgg   2400
cgagggcgag ggcgatgcca cctacggcaa gctgaccctg aagttcatct gcaccaccgg   2460
caagctgccc gtgccctggc ccaccctcgt gaccaccttc acctacggcg tgcagtgctt   2520
cagccgctac cccgaccaca tgaagcagca cgacttcttc aagtccgcca tgcccgaagg   2580
ctacgtccag gagcgcacca tcttcttcaa ggacgacggc aactacaaga cccgcgccga   2640
ggtgaagttc gagggcgaca cctggtgaa ccgcatcgag ctgaagggca tcgacttcaa   2700
ggaggacggc aacatcctgg ggcacaagct ggagtacaac tacaacagcc acaacgtcta   2760
tatcatggcc gacaagcaga gaacggcat caaggtgaac ttcaagatcc gccacaacat   2820
cgaggacggc agcgtgcagc tcgccgacca ctaccagcag aacacccca tcggcgacgg   2880
ccccgtgctg ctgcccgaca accactacct gagcacccag tccgccctga gcaaagaccc   2940
caacgagaag cgcgatcaca tggtcctgct ggagttcgtg accgccgccg ggatcactct   3000
cggcatggac gagctgtaca agtaatgaat taattaagaa ttgcggccgc gtcgacctgc   3060
```

```
agccaagctt atcgataaaa taaaagattt tatttagtct ccagaaaaag gggggaatga    3120
aagaccccac ctgtaggttt ggcaagaatt cgtttaaacg ggctcgagtg gtctcataca    3180
gaacttataa gattcccaaa tccaaagaca tttcacgttt atggtgattt cccagaacac    3240
atagcgacat gcaaatattg ggatccgcta gcttaagtaa cgccattttg caaggcatgg    3300
aaaatacata actgagaata gagaagttca gatcaaggtt aggaacagag agacagcaga    3360
atatgggcca aacaggatat ctgtggtaag cagttcctgc cccggctcag ggccaagaac    3420
agatggtccc cagatgcggt cccgccctca gcagtttcta gagaaccatc agatgtttcc    3480
agggtgcccc aaggacctga aaatgaccct gtgccttatt tgaactaacc aatcagttcg    3540
cttctcgctt ctgttcgcgc gcttctgctc cccgagctca ataaaagagc ccacaacccc    3600
tcactcggcg cgccagtcct ccgatagact gcgtcgcccg ggtacccgtg tatccaataa    3660
accctcttgc agttgcatcc gacttgtggt ctcgctgttc cttgggaggg tctcctctga    3720
gtgattgact acccgtcagc gggggtcttt catgggtaac agtttcttga agttggagaa    3780
caacattctg agggtaggag tcgaatatta agtaatcctg actcaattag ccactgtttt    3840
gaatccacat actccaatac tcctgaaata gttcattatg gacagcgcag aagagctggg    3900
gagaattaat tcgtaatcat ggtcatagct gtttcctgtg tgaaattgtt atccgctcac    3960
aattccacac aacatacgag ccggaagcat aaagtgtaaa gcctggggtg cctaatgagt    4020
gagctaactc acattaattg cgttgcgctc actgcccgct ttccagtcgg gaaacctgtc    4080
gtgccagctg cattaatgaa tcggccaacg cgcggggaga ggcggtttgc gtattgggcg    4140
ctcttccgct tcctcgctca ctgactcgct gcgctcggtc gttcggctgc ggcgagcggt    4200
atcagctcac tcaaaggcgg taatacggtt atccacagaa tcaggggata acgcaggaaa    4260
gaacatgtga gcaaaaggcc agcaaaaggc caggaaccgt aaaaaggccg cgttgctggc    4320
gtttttccat aggctccgcc cccctgacga gcatcacaaa aatcgacgct caagtcagag    4380
gtggcgaaac ccgacaggac tataaagata ccaggcgttt ccccctggaa gctccctcgt    4440
gcgctctcct gttccgaccc tgccgcttac cggatacctg tccgcctttc tcccttcggg    4500
aagcgtggcg ctttctcata gctcacgctg taggtatctc agttcggtgt aggtcgttcg    4560
ctccaagctg ggctgtgtgc acgaaccccc cgttcagccc gaccgctgcg ccttatccgg    4620
taactatcgt cttgagtcca acccggtaag acacgactta tcgccactgg cagcagccac    4680
tggtaacagg attagcagag cgaggtatgt aggcggtgct acagagttct tgaagtggtg    4740
gcctaactac ggctacacta aggacagt atttggtatc tgcgctctgc tgaagccagt    4800
taccttcgga aaaagagttg gtagctcttg atccggcaaa caaaccaccg ctggtagcgg    4860
tggttttttt gtttgcaagc agcagattac gcgcagaaaa aaggatctc aagaagatcc    4920
tttgatcttt tctacggggt ctgacgctca gtggaacgaa aactcacgtt aagggatttt    4980
ggtcatgaga ttatcaaaaa ggatcttcac ctagatcctt ttaaattaaa aatgaagttt    5040
taaatcaatc taaagtatat atgagtaaac ttggtctgac agttaccaat gcttaatcag    5100
tgaggcacct atctcagcga tctgtctatt tcgttcatcc atagttgcct gactccccgt    5160
cgtgtagata actacgatac gggagggctt accatctggc cccagtgctg caatgatacc    5220
gcgagaccca cgctcaccgg ctccagattt atcagcaata aaccagccag ccggaagggc    5280
cgagcgcaga agtggtcctg caactttatc cgcctccatc cagtctatta attgttgccg    5340
ggaagctaga gtaagtagtt cgccagttaa tagtttcgc aacgttgttg ccattgctac    5400
aggcatcgtg gtgtcacgct cgtcgtttgg tatggcttca ttcagctccg gttcccaacg    5460
```

```
atcaaggcga gttacatgat cccccatgtt gtgcaaaaaa gcggttagct ccttcggtcc      5520
tccgatcgtt gtcagaagta agttggccgc agtgttatca ctcatggtta tggcagcact      5580
gcataattct cttactgtca tgccatccgt aagatgcttt tctgtgactg gtgagtactc      5640
aaccaagtca ttctgagaat agtgtatgcg gcgaccgagt tgctcttgcc cggcgtcaat      5700
acgggataat accgcgccac atagcagaac tttaaaagtg ctcatcattg gaaaacgttc      5760 ttcgggggcga aaactctcaa ggatcttacc gctgttgaga tccagttcga tgtaacccac      5820
tcgtgcaccc aactgatctt cagcatcttt tactttcacc agcgtttctg ggtgagcaaa      5880
aacaggaagg caaaatgccg caaaaaaggg aataagggcg cacggaaat gttgaatact       5940 catactcttc cttttcaat attattgaag catttatcag ggttattgtc tcatgagcgg       6000
atacatattt gaatgtattt agaaaaataa acaaataggg gttccgcgca catttccccg      6060
aaaagtgcca cctgacgtct aagaaaccat tattatcatg acattaacct ataaaaatag      6120
gcgtatcacg aggcccttt c gtctcgcgcg tttcggtgat gacggtgaaa acctctgaca     6180
catgcagctc ccggagacgg tcacagcttg tctgtaagcg gatgccggga gcagacaagc      6240
ccgtcagggc gcgtcagcgg gtgttggcgg gtgtcggggc tggcttaact atgcggcatc      6300
agagcagatt gtactgagag tgcaccatat gcggtgtgaa ataccgcaca gatgcgtaag      6360
gagaaaatac cgcatcaggc gccattcgcc attcaggctg cgcaactgtt gggaagggcg      6420
atcggtgcgg gcctcttcgc tattacgcca gctggcgaaa gggggatgtg ctgcaaggcg      6480
attaagttgg gtaacgccag ggttttccca gtcacgacgt tgtaaaacga cggccagtgc      6540
caagctcgct ctcccttatg cgactcctgc attaggaagc agcccagtag taggttgagg      6600
ccgttgagca ccgccgccgc aaggaatggt gcatgcaagg agatggcgcc caacagtccc      6660
ccggccacgg ggcctgccac catacccacg ccgaaacaag cgctcatgag cccgaagtgg      6720
cgagcccgat cttcccccatc ggtgatgtcg gcgatatagg cgccagcaac cgcacctgtg      6780
gcgccggtga tgccggccac gatgcgtccg gcgtagagga tcgattagtc caatttgtta      6840
aagacaggat atcagtggtc caggctctag ttttgactca acaatatcac cagctgaagc      6900
ctatagagta cgagccatag ataaaataaa agattttatt tagtctccag aaaaagggggg      6960 gaa                                                                    6963

<210> SEQ ID NO 2
<211> LENGTH: 23
<212> TYPE: DNA
<213> ORGANISM: Artificial sequence
<220> FEATURE:
<223> OTHER INFORMATION: Synthetic microRNA

<400> SEQUENCE: 2
caaagtgctg ttcgtgcagg tag                                              23

<210> SEQ ID NO 3
<211> LENGTH: 16
<212> TYPE: DNA
<213> ORGANISM: Artificial sequence
<220> FEATURE:
<223> OTHER INFORMATION: Synthetic microRNA

<400> SEQUENCE: 3
gcaggcaaaa ccccaa                                                      16

<210> SEQ ID NO 4
<211> LENGTH: 21
```

```
<212> TYPE: DNA
<213> ORGANISM: Artificial sequence
<220> FEATURE:
<223> OTHER INFORMATION: Synthetic microRNA

<400> SEQUENCE: 4
aacattcaac gctgtcggtg a                                              21

<210> SEQ ID NO 5
<211> LENGTH: 19
<212> TYPE: DNA
<213> ORGANISM: Artificial sequence
<220> FEATURE:
<223> OTHER INFORMATION: Synthetic microRNA

<400> SEQUENCE: 5
cccaaaagag aaagcacac                                                 19

<210> SEQ ID NO 6
<211> LENGTH: 22
<212> TYPE: DNA
<213> ORGANISM: Artificial sequence
<220> FEATURE:
<223> OTHER INFORMATION: Synthetic microRNA

<400> SEQUENCE: 6
tgtaaacatc ctacactcag ct                                             22

<210> SEQ ID NO 7
<211> LENGTH: 13
<212> TYPE: DNA
<213> ORGANISM: Artificial sequence
<220> FEATURE:
<223> OTHER INFORMATION: Synthetic microRNA

<400> SEQUENCE: 7
gaggagaggg agg                                                       13

<210> SEQ ID NO 8
<211> LENGTH: 13
<212> TYPE: DNA
<213> ORGANISM: Artificial sequence
<220> FEATURE:
<223> OTHER INFORMATION: Synthetic microRNA

<400> SEQUENCE: 8
gaggagagga cag                                                       13

<210> SEQ ID NO 9
<211> LENGTH: 15
<212> TYPE: DNA
<213> ORGANISM: Artificial sequence
<220> FEATURE:
<223> OTHER INFORMATION: Synthetic microRNA

<400> SEQUENCE: 9
agcagcacaa agggg                                                     15

<210> SEQ ID NO 10
<211> LENGTH: 17
<212> TYPE: DNA
<213> ORGANISM: Artificial sequence
<220> FEATURE:
<223> OTHER INFORMATION: Synthetic microRNA

<400> SEQUENCE: 10
agcagcacga aaaggcg                                                   17
```

```
<210> SEQ ID NO 11
<211> LENGTH: 18
<212> TYPE: DNA
<213> ORGANISM: Artificial sequence
<220> FEATURE:
<223> OTHER INFORMATION: Synthetic microRNA

<400> SEQUENCE: 11
ggcaaaccag caaaacga                                                 18

<210> SEQ ID NO 12
<211> LENGTH: 16
<212> TYPE: DNA
<213> ORGANISM: Artificial sequence
<220> FEATURE:
<223> OTHER INFORMATION: Synthetic microRNA

<400> SEQUENCE: 12
aaaggcaagg caggag                                                   16

<210> SEQ ID NO 13
<211> LENGTH: 16
<212> TYPE: DNA
<213> ORGANISM: Artificial sequence
<220> FEATURE:
<223> OTHER INFORMATION: Synthetic microRNA

<400> SEQUENCE: 13
acacagccag ggacca                                                   16

<210> SEQ ID NO 14
<211> LENGTH: 14
<212> TYPE: DNA
<213> ORGANISM: Artificial sequence
<220> FEATURE:
<223> OTHER INFORMATION: Synthetic microRNA

<400> SEQUENCE: 14
cacagggcaa gcgc                                                     14

<210> SEQ ID NO 15
<211> LENGTH: 16
<212> TYPE: DNA
<213> ORGANISM: Artificial sequence
<220> FEATURE:
<223> OTHER INFORMATION: Synthetic microRNA

<400> SEQUENCE: 15
agcaccacga aacgga                                                   16

<210> SEQ ID NO 16
<211> LENGTH: 17
<212> TYPE: DNA
<213> ORGANISM: Artificial sequence
<220> FEATURE:
<223> OTHER INFORMATION: Synthetic microRNA

<400> SEQUENCE: 16
gaaacaccac acccagc                                                  17

<210> SEQ ID NO 17
<211> LENGTH: 15
<212> TYPE: DNA
<213> ORGANISM: Artificial sequence
<220> FEATURE:
<223> OTHER INFORMATION: Synthetic microRNA
```

```
<400> SEQUENCE: 17
agcacagacg aggac                                                        15

<210> SEQ ID NO 18
<211> LENGTH: 20
<212> TYPE: DNA
<213> ORGANISM: Artificial sequence
<220> FEATURE:
<223> OTHER INFORMATION: Synthetic microRNA

<400> SEQUENCE: 18
caacggaacc caaaagcagc                                                   20

<210> SEQ ID NO 19
<211> LENGTH: 17
<212> TYPE: DNA
<213> ORGANISM: Artificial sequence
<220> FEATURE:
<223> OTHER INFORMATION: Synthetic microRNA

<400> SEQUENCE: 19
ccgacgagcg ccccgag                                                      17

<210> SEQ ID NO 20
<211> LENGTH: 15
<212> TYPE: DNA
<213> ORGANISM: Artificial sequence
<220> FEATURE:
<223> OTHER INFORMATION: Synthetic microRNA

<400> SEQUENCE: 20
aaaagcaaga gacga                                                        15

<210> SEQ ID NO 21
<211> LENGTH: 12
<212> TYPE: DNA
<213> ORGANISM: Artificial sequence
<220> FEATURE:
<223> OTHER INFORMATION: Synthetic microRNA

<400> SEQUENCE: 21
gaggaagggc ga                                                           12

<210> SEQ ID NO 22
<211> LENGTH: 21
<212> TYPE: DNA
<213> ORGANISM: Artificial sequence
<220> FEATURE:
<223> OTHER INFORMATION: Synthetic microRNA

<400> SEQUENCE: 22
accacaggga gaaccacgga c                                                 21

<210> SEQ ID NO 23
<211> LENGTH: 163
<212> TYPE: RNA
<213> ORGANISM: Artificial sequence
<220> FEATURE:
<223> OTHER INFORMATION: Synthetic precursor microRNA
<220> FEATURE:
<221> NAME/KEY: misc_feature
<222> LOCATION: (1)..(40)
<223> OTHER INFORMATION: wherein n is any nucleotide and wherein any one
      or more may be missing
<220> FEATURE:
<221> NAME/KEY: misc_feature
<222> LOCATION: (47)..(74)
```

```
<223> OTHER INFORMATION: wherein n is any nucleotide and any 1 to 12 n's
      may be deleted
<220> FEATURE:
<221> NAME/KEY: misc_feature
<222> LOCATION: (89)..(116)
<223> OTHER INFORMATION: wherein n is any nucleotide and any 1 to 12 n's
      may be deleted
<220> FEATURE:
<221> NAME/KEY: misc_feature
<222> LOCATION: (124)..(163)
<223> OTHER INFORMATION: wherein n is any nucleotide and wherein any one
      or more may be missing

<400> SEQUENCE: 23
nnnnnnnnnn nnnnnnnnnn nnnnnnnnnn nnnnnnnnnn gcuccannnn nnnnnnnnn        60 nnnnnnnnnn nnnnuguaau uaccugacnn nnnnnnnnnn nnnnnnnnnn nnnnnncccg       120
agcnnnnnnn nnnnnnnnnn nnnnnnnnnn nnnnnnnnnn nnn                        163

<210> SEQ ID NO 24
<211> LENGTH: 64
<212> TYPE: RNA
<213> ORGANISM: Artificial sequence
<220> FEATURE:
<223> OTHER INFORMATION: Synthetic microRNA

<400> SEQUENCE: 24
uccaaagugc uguucgugca gguaguguaa uuaccugacc uacugcugag cuagcacuuc        60
ccga                                                                    64

<210> SEQ ID NO 25
<211> LENGTH: 78
<212> TYPE: RNA
<213> ORGANISM: Artificial sequence
<220> FEATURE:
<223> OTHER INFORMATION: Synthetic microRNA

<400> SEQUENCE: 25 uggggggcucc aaagugcugu ucgugcaggu aguguaauua ccugaccuac ugcugagcua       60
gcacuucccg agccccca                                                     78

<210> SEQ ID NO 26
<211> LENGTH: 11
<212> TYPE: DNA
<213> ORGANISM: Artificial sequence
<220> FEATURE:
<223> OTHER INFORMATION: Synthetic microRNA
<220> FEATURE:
<223> OTHER INFORMATION: Synthetic DNA/microRNA

<400> SEQUENCE: 26
ctcgagcucc a                                                            11

<210> SEQ ID NO 27
<211> LENGTH: 14
<212> TYPE: DNA
<213> ORGANISM: Artificial sequence
<220> FEATURE:
<223> OTHER INFORMATION: Synthetic microRNA
<220> FEATURE:
<223> OTHER INFORMATION: Synthetic DNA/microRNA

<400> SEQUENCE: 27
uguaauuacc ugac                                                         14

<210> SEQ ID NO 28
<211> LENGTH: 12
```

```
<212> TYPE: DNA
<213> ORGANISM: Artificial sequence
<220> FEATURE:
<223> OTHER INFORMATION: Synthetic microRNA
<220> FEATURE:
<223> OTHER INFORMATION: Synthetic DNA/microRNA

<400> SEQUENCE: 28
cccgagctcg ag                                                    12
```